US008513209B2

(12) United States Patent
Olson et al.

(10) Patent No.: US 8,513,209 B2
(45) Date of Patent: Aug. 20, 2013

(54) MICRO-RNAS OF THE MIR-15 FAMILY MODULATE CARDIOMYOCYTE SURVIVAL AND CARDIAC REPAIR

(75) Inventors: Eric Olson, Dallas, TX (US); Eva van Rooij, Boulder, CO (US)

(73) Assignee: The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/742,233

(22) PCT Filed: Nov. 10, 2008

(86) PCT No.: PCT/US2008/083020
§ 371 (c)(1),
(2), (4) Date: Aug. 24, 2010

(87) PCT Pub. No.: WO2009/062169
PCT Pub. Date: May 14, 2009

(65) Prior Publication Data
US 2010/0317713 A1 Dec. 16, 2010

Related U.S. Application Data

(60) Provisional application No. 60/986,798, filed on Nov. 9, 2007.

(51) Int. Cl.
*A61K 48/00* (2006.01)
(52) U.S. Cl.
USPC ......... 514/44; 536/24.5; 536/24.1; 536/24.31
(58) Field of Classification Search
None
See application file for complete search history.

(56) References Cited

U.S. PATENT DOCUMENTS

| | | | |
|---|---|---|---|
| 7,232,806 B2 | 6/2007 | Tuschl et al. | |
| 7,482,117 B2 | 1/2009 | Cargill et al. | |
| 7,582,744 B2 | 9/2009 | Manoharan et al. | |
| 7,759,319 B2 * | 7/2010 | Lollo et al. ................. | 514/44 R |
| 2005/0026169 A1 | 2/2005 | Cargill et al. | |
| 2005/0059005 A1 | 3/2005 | Tuschl et al. | |
| 2005/0075492 A1 | 4/2005 | Chen et al. | |
| 2005/0182011 A1 | 8/2005 | Olson et al. | |
| 2006/0058266 A1 | 3/2006 | Manoharan et al. | |
| 2006/0105360 A1 | 5/2006 | Croce et al. | |
| 2006/0165659 A1 | 7/2006 | Croce et al. | |
| 2006/0185027 A1 | 8/2006 | Bartel et al. | |
| 2006/0189557 A1 | 8/2006 | Slack et al. | |
| 2006/0247193 A1 | 11/2006 | Taira et al. | |
| 2006/0252722 A1 | 11/2006 | Lollo et al. | |
| 2007/0026403 A1 | 2/2007 | Hatzigeorgiou et al. | |
| 2007/0054287 A1 | 3/2007 | Bloch | |
| 2007/0213292 A1 | 9/2007 | Stoffel et al. | |
| 2007/0259827 A1 | 11/2007 | Aronin et al. | |
| 2007/0287179 A1 | 12/2007 | Tuschl et al. | |
| 2007/0292878 A1 | 12/2007 | Raymond | |
| 2008/0050744 A1 | 2/2008 | Brown et al. | |
| 2008/0176766 A1 | 7/2008 | Brown et al. | |

| | | | |
|---|---|---|---|
| 2008/0220423 A1 | 9/2008 | Moller et al. | |
| 2009/0053718 A1 | 2/2009 | Naguibneva et al. | |
| 2009/0092980 A1 | 4/2009 | Arenz et al. | |
| 2009/0131356 A1 | 5/2009 | Bader et al. | |
| 2009/0176723 A1 | 7/2009 | Brown et al. | |
| 2009/0214477 A1 | 8/2009 | Betz et al. | |
| 2009/0221685 A1 | 9/2009 | Esau et al. | |
| 2009/0226528 A1 | 9/2009 | Czech et al. | |
| 2009/0281167 A1 | 11/2009 | Shen et al. | |
| 2009/0286969 A1 | 11/2009 | Esau et al. | |
| 2009/0286973 A1 | 11/2009 | Manoharan et al. | |
| 2009/0291906 A1 | 11/2009 | Esau et al. | |
| 2009/0291907 A1 | 11/2009 | Esau et al. | |
| 2009/0293148 A1 | 11/2009 | Ren et al. | |
| 2009/0298174 A1 * | 12/2009 | Esau et al. ..................... | 435/375 |
| 2009/0306181 A1 * | 12/2009 | Ikeda et al. ................. | 514/44 A |
| 2009/0326049 A1 | 12/2009 | Aristarkhov et al. | |
| 2010/0029003 A1 | 2/2010 | Bartel et al. | |
| 2010/0069471 A1 | 3/2010 | Manoharan et al. | |
| 2010/0087512 A1 | 4/2010 | Tuschl et al. | |
| 2010/0087513 A1 | 4/2010 | Tuschl et al. | |
| 2010/0093837 A1 | 4/2010 | Tuschl et al. | |
| 2010/0099748 A1 | 4/2010 | Tuschl et al. | |
| 2010/0113284 A1 | 5/2010 | Aristarkhov et al. | |
| 2010/0113561 A1 | 5/2010 | Tuschl et al. | |

FOREIGN PATENT DOCUMENTS

| | | |
|---|---|---|
| EP | 1627925 A1 | 2/2006 |
| EP | 1676914 A1 | 7/2006 |
| EP | 1777301 A2 | 4/2007 |
| EP | 1959012 A2 | 8/2008 |
| EP | 2105145 A1 | 9/2009 |
| EP | 2113567 A1 | 11/2009 |
| JP | 2006-506469 | 2/2006 |
| JP | 2006-519008 | 8/2006 |

(Continued)

OTHER PUBLICATIONS

Lagos-Quintana et al.,"New microRNAs from mouse and human," RNA, vol. 9: 175-179, 2003.
Lagos-Quintana et al., "Identification of tissue-specific microRNAs from mouse," Current Biology, vol. 12:735-739, 2002.
Sempere et al., "Expression profiling of mammalian microRNAs uncovers a subset of brain-expressed microRNAs with possible roles in murine and human neuronal differentiation," Genome Biology, vol. 5:R13, 2004.
Van Rooij et al., "A signature patter of stress-responsive microRNAs that can evoke cardiac hypertrophy and heart failure," Proc. Natl. Acad. Sci. USA, vol. 103: 18255-18260, 2006.
Landgraf et al., "A mammalian microRNA expression atlas based on small RNA library sequencing," Cell, vol. 129, 1401-1414, 2007.
Landgraf et al., "A mammalian microRNA expression atlas based on small RNA library sequencing," Cell, Supplementary Tables S12, 2007.

(Continued)

*Primary Examiner* — Kimberly Chong
(74) *Attorney, Agent, or Firm* — Cooley LLP

(57) ABSTRACT

A family of microRNAs, called the miR-15 family, which includes miR-195, are shown to be up-regulated during pathological cardiac remodeling and repress the expression of mRNAs required for cell proliferation and survival, with consequent loss of cardiomyocytes. Strategies to block expression of the miR-15 family in the heart as a treatment for diverse cardiac disease are provided.

27 Claims, 9 Drawing Sheets

(56) References Cited

FOREIGN PATENT DOCUMENTS

| | | |
|---|---|---|
| JP | 2006-292367 | 10/2006 |
| WO | WO 03/029459 A2 | 4/2003 |
| WO | WO 03/093441 A2 | 11/2003 |
| WO | WO 2004/043387 A2 | 5/2004 |
| WO | WO 2004/076622 A2 | 9/2004 |
| WO | WO 2005/013901 A2 | 2/2005 |
| WO | WO 2005/017145 A1 | 2/2005 |
| WO | WO 2005/040419 A1 | 5/2005 |
| WO | WO 2005/056797 A1 | 6/2005 |
| WO | WO 2005/078096 A2 | 8/2005 |
| WO | WO 2005/078139 A2 | 8/2005 |
| WO | WO 2005/097205 A2 | 10/2005 |
| WO | WO 2005/098029 A2 | 10/2005 |
| WO | WO 2005/118806 A2 | 12/2005 |
| WO | WO 2006/020768 A2 | 2/2006 |
| WO | WO 2006/048553 A1 | 5/2006 |
| WO | WO 2006/063356 A1 | 6/2006 |
| WO | WO 2006/071884 A2 | 7/2006 |
| WO | WO 2006/108473 A1 | 10/2006 |
| WO | WO 2006/111512 A1 | 10/2006 |
| WO | WO 2006/133022 A2 | 12/2006 |
| WO | WO 2006/137941 A2 | 12/2006 |
| WO | WO 2007/000668 A2 | 1/2007 |
| WO | WO 2007/021896 A2 | 2/2007 |
| WO | WO 2007/033023 A2 | 3/2007 |
| WO | WO 2007/044362 A2 | 4/2007 |
| WO | WO 2007/053184 A2 | 5/2007 |
| WO | WO 2007/056826 A1 | 5/2007 |
| WO | WO 2007/087451 A2 | 8/2007 |
| WO | WO 2007/089607 A2 | 8/2007 |
| WO | WO 2007/090073 A2 | 8/2007 |
| WO | WO 2007/092181 A2 | 8/2007 |
| WO | WO 2007/092182 A2 | 8/2007 |
| WO | WO 2007/095387 A2 | 8/2007 |
| WO | WO 2007/103808 A2 | 9/2007 |
| WO | WO 2007/112754 A2 | 10/2007 |
| WO | WO 2007/147067 A2 | 12/2007 |
| WO | WO 2007/147409 A2 | 12/2007 |
| WO | WO 2008/024499 A2 | 2/2008 |
| WO | WO 2008/036776 A2 | 3/2008 |
| WO | WO 2008/042231 A2 | 4/2008 |
| WO | WO 2008/043521 A2 | 4/2008 |
| WO | WO 2008/061537 A2 | 5/2008 |
| WO | WO 2008/073920 A2 | 6/2008 |
| WO | WO 2008/073921 A2 | 6/2008 |
| WO | WO 2008/073922 A2 | 6/2008 |
| WO | WO 2008/073923 A2 | 6/2008 |
| WO | WO 2008/074328 A2 | 6/2008 |
| WO | WO 2008/085797 A2 | 7/2008 |
| WO | WO 2008/112226 A2 | 9/2008 |
| WO | WO 2008/116267 A1 | 10/2008 |
| WO | WO 2008/147430 A2 | 12/2008 |
| WO | WO 2008/147839 A1 | 12/2008 |
| WO | WO 2009/012263 A2 | 1/2009 |
| WO | WO 2009/043353 A2 | 4/2009 |
| WO | WO 2009/044895 A1 | 4/2009 |
| WO | WO 2009/058818 A2 | 5/2009 |
| WO | WO 2009/062169 A2 | 5/2009 |
| WO | WO 2009/121031 A1 | 10/2009 |
| WO | WO 2009/149182 A1 | 12/2009 |
| WO | WO 2010/036939 A2 | 4/2010 |
| WO | WO 2010/048585 A2 | 4/2010 |

OTHER PUBLICATIONS

Van Rooij et al., "Control of stress-dependent cardiac growth and gene expression by a microRNA," Science, vol. 316: 575-579, 2007.

Van Rooij et al., "MicroRNA function during cardiac hypertrophy," Abstract and Poster from 3rd Annual Symposium of the American Heart Association Council on Basic Cardiovascular Sciences: Translation of Basic Insights Into Clinical Practice: Jul. 31-Aug. 3, 2006 Keystone Conference Ceneter Keystone, CO.

Ping et al., "The Study and Use of Antisens Oligonucleotide Technique in Cardiovascular Disease," Chinese Journal of Clinical Pharmacology and Therapeutics, vol. 11: 241-245, 2006.

English Translation of Examination Report for Chinese Application No. 200880124495.1 issued Nov. 14, 2011.

Seranski, Supplementary European Search Report and Opinion for European Application No. 08847645.2, 9 pages, European Patent Office, Munich, mailed Jan. 27, 2012.

Young, Written Opinion of the International Search Authority for PCT/US2008/083020, 7 pages, mailed May 13, 2009.

Young, "International Search Report," 4 pages, from International Patent Application No. PCT/US08/83020, USPTO, Alexandria, Virginia, US (mailed May 13, 2009).

* cited by examiner

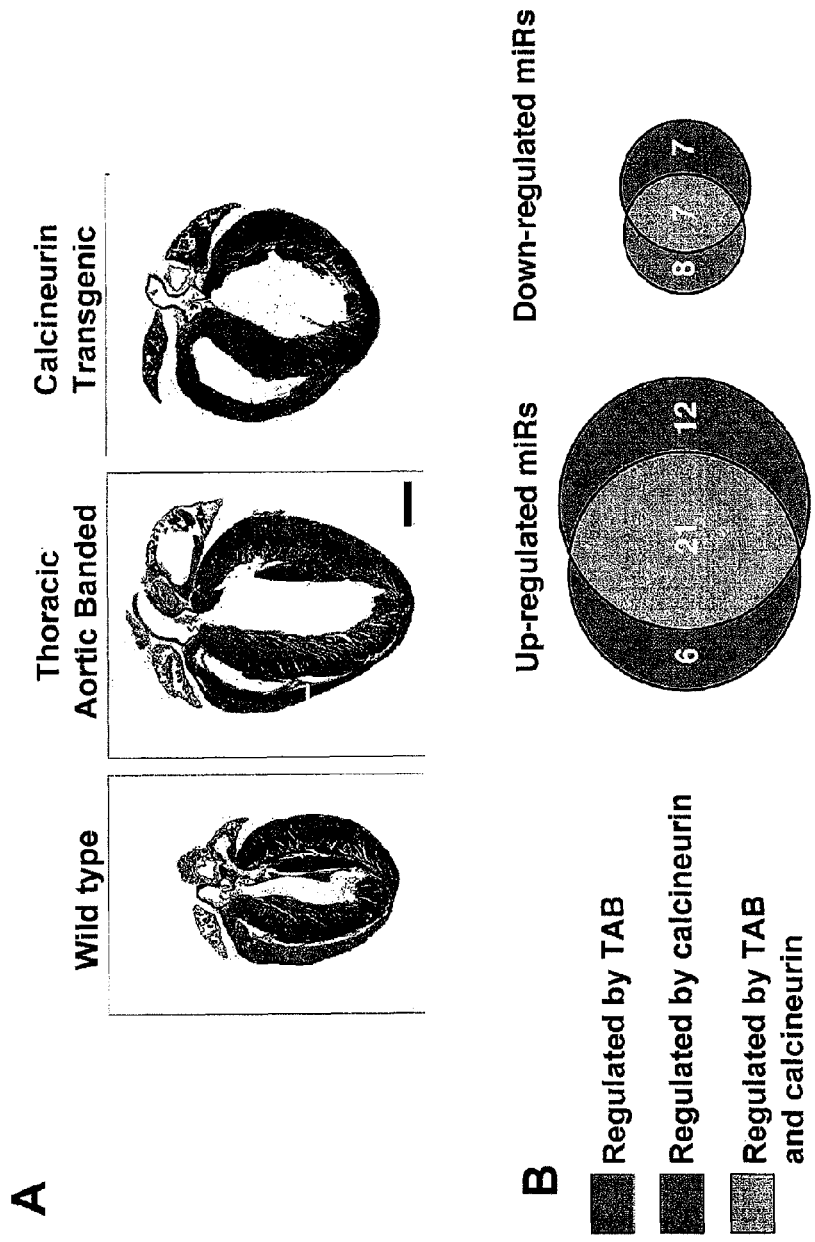
Figure 1A-B

Figure 4A-C

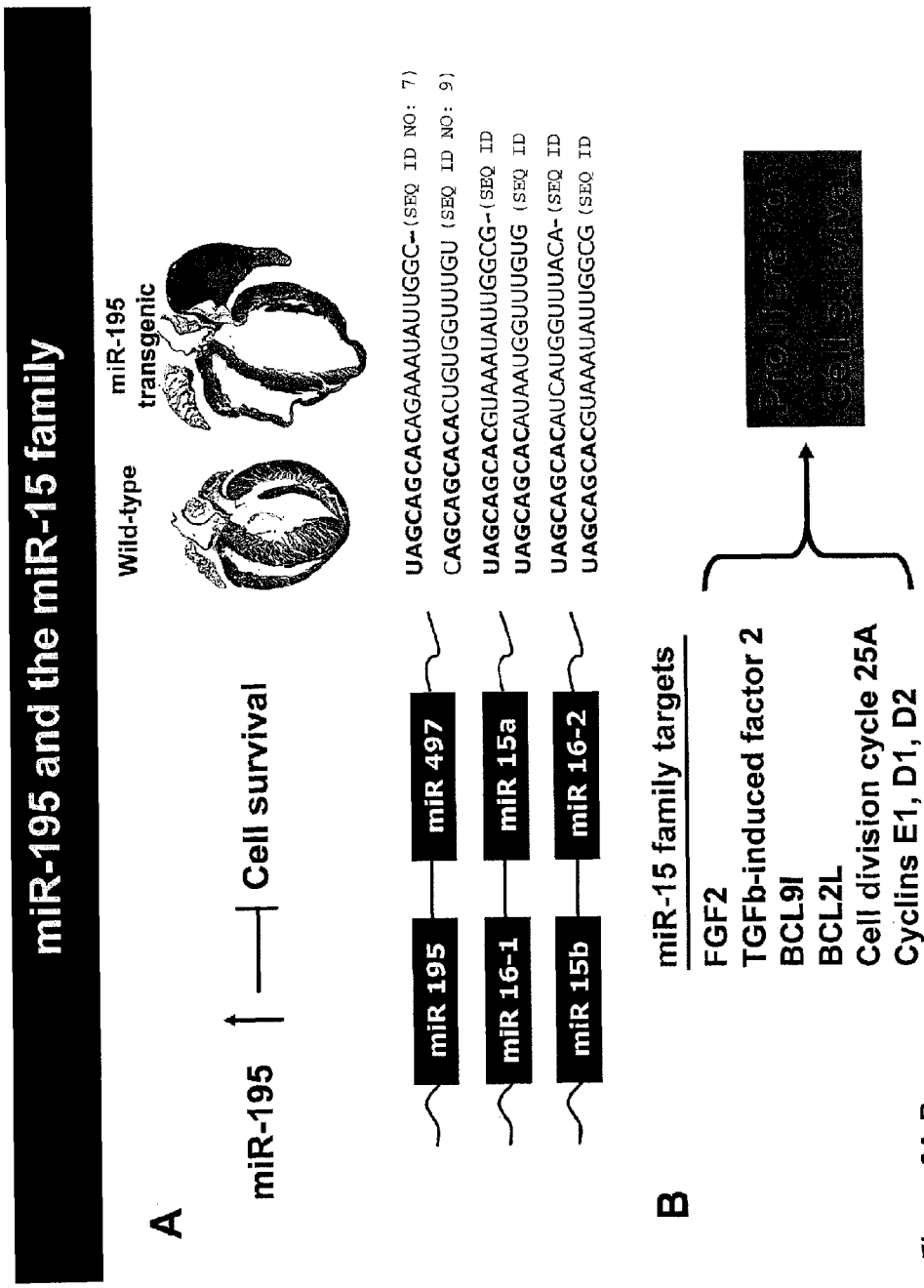
Figure 6A-B

FGF2 predicted target for miR-195

3'UTR FGF2

Gene
Human FGF2 3' UTR length:5385

Conserved sites for conserved miRNA families miR-140
miR-15/16/195
miR-103/107
miR-503
miR-15/16/195/
miR-503

(SEQ ID NO: 19) CGGUUAUAAAGACACGACGAU        (SEQ ID NO: 19) CGGUUAUAAAGACACGACGAU (SEQ ID NO: 20) Human   AAAATATTTTGCTGCTAGTTAACTA-TGAACAGATAGAAGAATCTTACAGATGCTGCTATAAATAAGTAG
(SEQ ID NO: 21) Mouse   ACGGAACTCAGCTGCTAGTTAACTA-TGAACCGATAG---GATTTTAGGATGCTGCTATGAGTAAGTAG
(SEQ ID NO: 22) Rat     ACAGAACTTCGCTGCTAGTTAACTA-TCGACAGATAG---GATCTTAAGATGCTGCTATGAGTAAGTA
(SEQ ID NO: 23) Dog     TTAAAATTTTGCTGCTAGTTAACTA-TTAACAGATAGAGGAATCATAACAGATGCTGCTATAAATAAG'

FGF2 function in the heart:

FGF-2 improves cell survival and decreases cardiac myocyte injury after an ischemic insult.

- Administration of exogenous FGF-2 before or during ischemic injury increases myocyte viability and functional recovery, and stimulated myocardial function and/or reduced infarct size through increase angiogenesis and systolic function

- Transgenic overexpression of FGF-2 in the heart increases myocyte viability following a period of gl( ischemia.

Figure 7

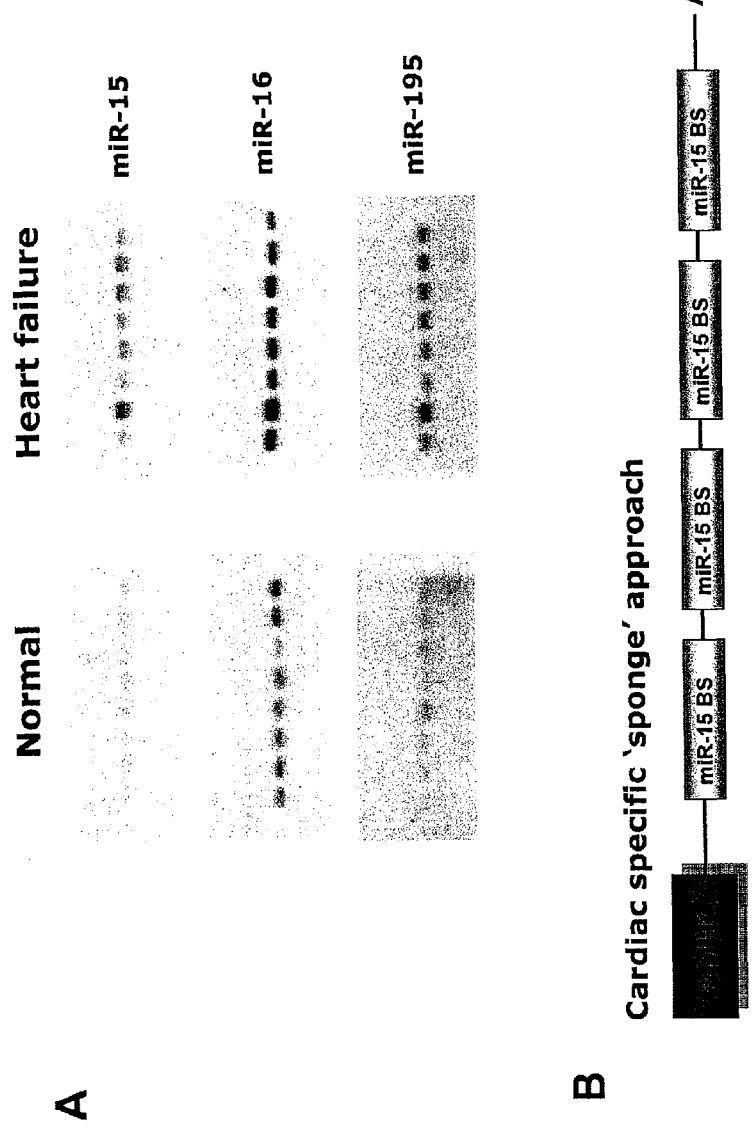
Figure 8A-B

MICRO-RNAS OF THE MIR-15 FAMILY MODULATE CARDIOMYOCYTE SURVIVAL AND CARDIAC REPAIR

CROSS-REFERENCE TO RELATED APPLICATIONS

This application is a national stage application of International Application No. PCT/US2008/083020, filed Nov. 10, 2008, which claims the benefit of U.S. Provisional Application No. 60/986,798, filed Nov. 9, 2007, which is herein incorporated by reference in its entirety.

STATEMENT OF GOVERNMENT SUPPORT

This invention was made with grant support under grant no. HL53351-06 from the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_002_01US_SeqList_ST25.txt, date recorded: Aug. 23, 2010, file size 4 kilobytes).

FIELD OF THE INVENTION

The present invention relates generally to the fields of developmental biology and molecular biology. More particularly, it concerns gene regulation and cellular physiology in cardiomyocytes. Specifically, the invention relates to a family of miRNAs, designated as the miR-15 family, that regulate cardiomyocyte survival and cardiac repair. Inhibition of these miRNAs provides for reduced apoptosis in cardiac cells and thus inhibits cardiac hypertrophy and heart failure.

BACKGROUND OF THE INVENTION

Heart disease and its manifestations, including coronary artery disease, myocardial infarction, congestive heart failure and cardiac hypertrophy, clearly present a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic.

With respect to cardiac hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to dilated cardiomyopathy (DCM), heart failure, and sudden death. In the United States, approximately half a million individuals are diagnosed with heart failure each year, with a mortality rate approaching 50%. The causes and effects of cardiac hypertrophy have been extensively documented, but the underlying molecular mechanisms have not been elucidated. Understanding these mechanisms is a major concern in the prevention and treatment of cardiac disease and will be crucial as a therapeutic modality in designing new drugs that specifically target cardiac hypertrophy and cardiac heart failure.

Treatment with pharmacological agents still represents the primary mechanism for reducing or eliminating the manifestations of heart failure. Diuretics constitute the first line of treatment for mild-to-moderate heart failure. If diuretics are ineffective, vasodilatory agents, such as angiotensin converting enzyme (ACE) inhibitors (e.g., enalapril and lisinopril) or inotropic agent therapy (i.e., a drug that improves cardiac output by increasing the force of myocardial muscle contraction) may be used. Unfortunately, many of these standard therapies have numerous adverse effects and are contraindicated in some patients. Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities.

The adult heart is a dynamic organ capable of significant remodeling and hypertrophic growth as a means of adapting function to altered workloads or injury. Hemodynamic stress or neuroendocrine signaling associated with myocardial infarction, hypertension, aortic stenosis, and valvular dysfunction evoke a pathologic remodeling response through the activation of intracellular signaling pathways and transcriptional mediators in cardiac myocytes. Activation of these molecular pathways enhances cardiomyocyte size and protein synthesis, induces the assembly of sarcomeres, and causes reexpression of fetal cardiac genes. Although aspects of the hypertrophic response after acute and chronic stress may initially augment cardiac output, prolonged hypertrophy is a major predictor of heart failure and sudden death. There have been major advances in the identification of genes and signaling pathways involved in this disease process, but the overall complexity of hypertrophic remodeling suggests that additional regulatory mechanisms remain to be identified.

MicroRNAs (miRNAs or miRs) have recently been implicated in a number of biological processes including regulation of developmental timing, apoptosis, fat metabolism, and hematopoietic cell differentiation among others. mRNAs are small, non-protein coding RNAs of about 18 to about 25 nucleotides in length that regulate gene expression in a sequence-specific manner mRNAs act as repressors of target mRNAs by promoting their degradation, when their sequences are perfectly complementary, or by inhibiting translation, when their sequences contain mismatches.

mRNAs are transcribed by RNA polymerase II (pol II) or RNA polymerase III (pol III; see Qi et al. (2006) Cellular & Molecular Immunology Vol. 3:411-419) and arise from initial transcripts, termed primary miRNA transcripts (pri-miRNAs), that are generally several thousand bases long and are derived from individual miRNA genes, from introns of protein coding genes, or from poly-cistronic transcripts that often encode multiple, closely related miRNAs. See review of Carrington et al. (2003). Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA (Lee et al., 1993). The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

The 5' portion of a miRNA spanning bases 2-8, termed the 'seed' region, is especially important for target recognition (Krenz and Robbins, 2004; Kiriazis and Kranias, 2000). The sequence of the seed, together with phylogenetic conservation of the target sequence, forms the basis for many current target prediction models. Although increasingly sophisticated computational approaches to predict miRNAs and their targets are becoming available, target prediction remains a major challenge and requires experimental validation. Ascribing the functions of miRNAs to the regulation of specific mRNA targets is further complicated by the ability of individual miRNAs to base pair with hundreds of potential high and low affinity mRNA targets and by the targeting of multiple miRNAs to individual mRNAs.

The high sequence conservation of many miRNAs across metazoan species suggests strong evolutionary pressure and participation in essential biologic processes (Reinhart et al., 2000; Stark et al., 2005). Indeed, miRNAs have been shown to play fundamental roles in diverse biological and pathological processes, including cell proliferation, differentiation, apoptosis, and carcinogenesis in species ranging from *Caenorhabditis elegans* and *Drosophila melanogaster* to humans. However, there remains limited information on the role that miRNAs play in cardiogenesis and molecular events that can contribute to heart disease.

SUMMARY OF THE INVENTION

The present invention provides a method of treating pathologic cardiac hypertrophy, heart failure, or myocardial infarction in a subject in need thereof. In one embodiment, the method comprises identifying a subject having cardiac hypertrophy, heart failure, or myocardial infarction; and inhibiting expression or activity of one or more miR-15 family members in heart cells of said subject. In another embodiment, the method further comprises administering to the subject a second therapy. The second therapy may be, for example, a beta blocker, an ionotrope, a diuretic, ACE inhibitor, AII antagonist, BNP, a Ca++-blocker, and ERA, or an HDAC inhibitor.

In some embodiments of the invention, inhibiting the expression or activity of one or more miR-15 family members comprises administering an antagomir of one or more miR-15 family members. In one embodiment, the expression or activity of one or more miR-15 family members is inhibited by administering an antisense oligonucleotide that targets the mature sequence of a miR-15 family member. In yet another embodiment, expression or activity of one or more miR-15 family members is inhibited by administering an inhibitory RNA molecule, wherein the inhibitory RNA molecule comprises a double stranded region that is at least partially identical and complementary to a mature sequence of a miR-15 family member. The inhibitory RNA molecule may be a ribozyme, siRNA or shRNA molecule. In still another embodiment, expression or activity of one or more miR-15 family members is inhibited by administering a nucleic acid comprising one or more miR-15 binding sites. A miR-15 binding site may comprise a sequence that is complementary to a seed sequence of miR-15. The one or more miR-15 family members may be miR-15a, miR-15b, miR-16-1, miR-16-2, miR-195, miR-424 and miR-497.

The present invention also provides a method of preventing pathologic hypertrophy or heart failure in a subject in need thereof. In one embodiment, the method comprises identifying a subject at risk of developing pathologic cardiac hypertrophy or heart failure; and inhibiting expression or activity of one or more miR-15 family members in heart cells of said subject. In one embodiment, inhibiting comprises delivering to the heart cells an inhibitor of one or more miR-15 family members. In another embodiment, the subject at risk may exhibit one or more risk factors selected from the group consisting of uncontrolled hypertension, uncorrected valvular disease, chronic angina, recent myocardial infarction, congenital predisposition to heart disease, and pathological hypertrophy.

Antagomirs, antisense oligonucleotides, inhibitory RNA molecules, nucleic acids comprising miR-15 binding sites or other modulators of the expression or activity of one or more miR-15 family members may be administered by any method known to those in the art suitable for delivery to the targeted organ, tissue, or cell type. For example, in certain embodiments of the invention, the modulator of one or more miR-15 family members may be administered by parenteral administration, such as intravenous injection, intraarterial injection, intrapericardial injection, or subcutaneous injection, or by direct injection into the tissue (e.g., cardiac tissue). In some embodiments, the modulator of one or more miR-15 family members may be administered by oral, transdermal, intraperitoneal, subcutaneous, sustained release, controlled release, delayed release, suppository, or sublingual routes of administration. In other embodiments, the modulator of one or more miR-15 family members may be administered by a catheter system.

The present invention also encompasses a transgenic, non-human mammal, the cells of which fail to express a functional form of one or more miR-15 family members (e.g. miR-15a, miR-15b, miR-16-1, miR-16-2, miR-195, miR-424 and miR-497). In another embodiment, the present invention includes a transgenic, non-human mammal, the cells of which comprise a coding region of a miR-15 family member under the control of a heterologous promoter active in the cells of said non-human mammal. In some embodiments, the mammal is a mouse.

The present invention provides a method for identifying a modulator of a miR-15 family member comprising (a) contacting a cell with a candidate compound; (b) assessing activity or expression of an miR-15 family member; and (c) comparing the activity or expression in step (b) with the activity or expression in the absence of the candidate compound, wherein a difference between the measured activities or expression indicates that the candidate compound is a modulator of said miR-15 family member. The cell may be contacted with the candidate compound in vitro or in vivo. The candidate compound may be a protein, a peptide, a polypeptide, a polynucleotide, an oligonucleotide, or small molecule. The modulator of a miR-15 family member may be an agonist or inhibitor of the miR-15 family member. The modulator of a miR-15 family member may be an agonist or inhibitor of an upstream regulator of the miR-15 family member.

The present invention also provides a pharmaceutical composition comprising an inhibitor of one or more miR-15 family members. In one embodiment, the composition is formulated for injection. In another embodiment, the pharmaceutical composition is combined with a kit for administration, such as parenteral or catheter administration.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6. MiR-195 is part of the miR-15 family that targets pro-survival proteins. A. MiR-195 is part of the miR-15 family that consists of five different miRs: miR-15, miR-16, miR-195, miR-424, and miR-497. Four of the miR-15 family members are expressed as three clusters of two miRNAs. B. MiR-15 family members target proteins involved in proliferation, survival and anti-apoptosis. Thus, up-regulation of miR-195 results in down-regulation of these mRNAs and cell death.

FIG. 7. MiR-195 target sequence in the 3' UTR of FGF2 mRNA.

FIG. 8. Enhanced expression of miR-15 family members in samples from failing human hearts. A. Left panel shows RNA blots from normal human hearts and right panel shows RNA blots from failing human hearts. B. The conserved seed region among miR-15 family members allows for an additional approach to knockdown the whole miR-15 family. This approach entails overexpression of multiple miR-15 binding sites under the control of a cardiac specific promoter, such as the alpha myosin heavy chain promoter (aMHC). Each of the miR-15 binding sites contains a sequence complementary to the sequence of the conserved seed region and allows for the scavenging of all family members, thereby preventing them from binding to their endogenous targets.

DETAILED DESCRIPTION OF ILLUSTRATIVE EMBODIMENTS

Figure 1C:
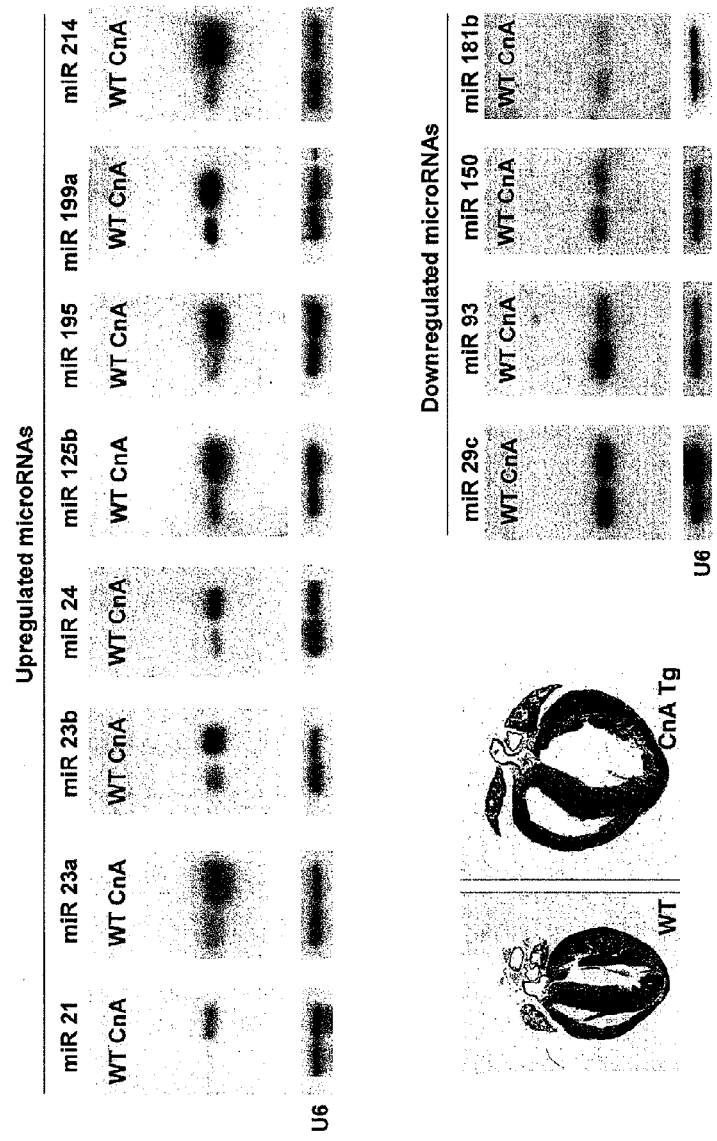
FIG. 1. miRNA expression during cardiac hypertrophy. A. H&E stained sections of representative hearts from mice following sham and thoracic aortic banding (TAB) for 21 days and from wild-type (WT) and activated calcineurin transgenic (CnA Tg) mice. Scale bar equals 2 mm. B. Numbers of miRNAs that were regulated in response to CnA or TAB are indicated. Although some changes were unique for either TAB or CnA-induced hypertrophy, most miRNAs that were induced or repressed overlapped for the different hypertrophic stimuli. C. Northern blot analysis of particular miRNAs in WT and CnA Tg hearts. U6 RNA was detected as a loading control.

The present invention is based, in part, on the discovery that members of the miR-15 family of microRNAs, such as miR-195, are upregulated in myocardial tissue from human failing hearts as well as in animal models of pathologic cardiac hypertrophy. Cardiac overexpression of miR-195 is sufficient to induce cardiac hypertrophy and can lead to a dilated phenotype. Accordingly, the present invention provides methods of treating or preventing various forms of heart disease in a subject by inhibiting the expression or activity of one or more members of the miR-15 family in heart cells of the subject.

The miR-15 family is a small family of microRNAs that includes miR-195, miR-16-1, miR-15a, miR-15b, miR-16-2, miR-424, and miR-497. Four of the miR-15 family members are expressed as three clustered transcripts (FIG. 6A). MiR-195 and miR-497 are expressed as a cluster from the intron of a gene located on chromosome 17. There are two copies of miR-16 located on different chromosomes. One copy (miR-16-1) is expressed as a cluster with miR-15a from an intron of a gene encoded on chromosome 13. The second copy (miR-16-2) is expressed as a cluster with 15b from the intron of the SMC4 gene located on chromosome 3. MiR-424 is expressed from the X chromosome. The pre-miRNA sequences (e.g. stem loop sequences) for each of the miR-15 family members are listed below:

```
Human pre-miR-195
                                            (SEQ ID NO: 1)
AGCUUCCCUG GCUCUAGCAG CACAGAAAUA UUGGCACAGG

GAAGCGAGUC UGCCAAUAUU GGCUGUGCUG CUCCAGGCAG

GGUGGUG

Human pre-miR-497
                                            (SEQ ID NO: 2)
CCACCCCGGU CCUGCUCCCG CCCCAGCAGC ACACUGUGGU

UUGUACGGCA CUGUGGCCAC GUCCAAACCA CACUGUGGUG

UUAGAGCGAG GGUGGGGGAG GCACCGCCGA GG

Human pre-miR-16-1
                                            (SEQ ID NO: 3)
GUCAGCAGUG CCUUAGCAGC ACGUAAAUAU UGGCGUUAAG

AUUCUAAAAU UAUCUCCAGU AUUAACUGUG CUGCUGAAGU

AAGGUUGAC

Human pre-miR-16-2
                                            (SEQ ID NO: 4)
GUUCCACUCU AGCAGCACGU AAAUAUUGGC GUAGUGAAAU

AUAUAUUAAA CACCAAUAUU ACUGUGCUGC UUUAGUGUGA C
```

-continued

Human pre-miR-15a
(SEQ ID NO: 5)
CCUUGGAGUA AAGUAGCAGC ACAUAAUGGU UUGUGGAUUU

UGAAAAGGUG CAGGCCAUAU UGUGCUGCCU CAAAAAUACA AGG

Human pre-miR-15b
(SEQ ID NO: 6)
UUGAGGCCUU AAAGUACUGU AGCAGCACAU CAUGGUUUAC

AUGCUACAGU CAAGAUGCGA AUCAUUAUUU GCUGCUCUAG

AAAUUUAAGG AAAUUCAU

Human pre-miR-424
(SEQ ID NO: 19)
CGAGGGAUA CAGCAGCAAU UCAUGUUUUG AAGUGUUCUA

AAUGGUUCAA AACGUGAGGC GCUGCUAUAC CCCCUCGUGG

GGAAGGUAGA AGGUGGGG

Each of the pre-miRNA sequences for each miR-15 family member is processed into a mature sequence and a star sequence. The star sequence is processed from the other strand of the stem loop structure. The mature and star sequences for each of the miR-15 family members is given below:

```
Human mature miR-195
UAGCAGCACAGAAAUAUUGGC           (SEQ ID NO: 7)

Human miR-195*
CCAAUAUUGGCUGUGCUGCUCC          (SEQ ID NO: 8)

Human mature miR-497
CAGCAGCACACUGUGGUUUGU           (SEQ ID NO: 9)

Human miR-497*
CAAACCACACUGUGGGUGUUAGA         (SEQ ID NO: 10)

Human mature miR-16-1/mlR-16-2
UAGCAGCACGUAAAUAUUGGCG          (SEQ ID NO: 11)

Human miR-16-1*
CCAGUAUUAACUGUGCUGCUGA          (SEQ ID NO: 12)

Human miR-16-2*
CCAAUAUUACUGUGCUGCUUUA          (SEQ ID NO: 13)

Human mature miR-15a
UAGCAGCACAUAAUGGUUUGUG          (SEQ ID NO: 14)

Human miR-15a*
CAGGCCAUAUUGUGCUGCCUCA          (SEQ ID NO: 15)

Human mature miR-15b
UAGCAGCACAUCAUGGUUUACA          (SEQ ID NO: 16)

Human miR-15b*
CGAAUCAUUAUUUGCUGCUCUA          (SEQ ID NO: 17)

Human mature miR-424
CAGCAGCAAUUCAUGUUUUGAA          (SEQ ID NO: 20)

Human miR-424*
CAAAACGUGAGGCGCUGCUAU           (SEQ ID NO: 21)
```

Although the seed region (e.g. bases spanning 2 to 8 nucleotides of mature miRNA sequence) for all family members is highly conserved (AGCAGCAC; SEQ ID NO: 18), the 3' end of the mature miRNA differs among the different family members (FIG. 6A).

The present invention provides a method of treating pathologic cardiac hypertrophy, heart failure, or myocardial infarction in a subject in need thereof by inhibiting expression or activity of one or more miR-15 family members. In one embodiment, the method comprises identifying a subject having cardiac hypertrophy, heart failure, or myocardial infarction; and inhibiting expression or activity of one or more miR-15 family members in heart cells of said subject. "Heart cells" as used herein include cardiomyocytes, cardiac fibroblasts, and cardiac endothelial cells. In another embodiment, the method comprises administering to the subject an inhibitor of one or more miR-15 family members. In still another embodiment, the method comprises identifying a subject at risk of developing pathologic cardiac hypertrophy or heart failure and inhibiting expression or activity of one or more miR-15 family members in heart cells of the subject. The subject at risk of developing pathologic cardiac hypertrophy or heart failure may exhibit one or more risk factors including, for example, uncontrolled hypertension, uncorrected valvular disease, chronic angina, recent myocardial infarction, congenital predisposition to heart disease or pathological hypertrophy. In certain embodiments, the subject at risk may be diagnosed as having a genetic predisposition to cardiac hypertrophy. In some embodiments of the invention, the subject at risk may have a familial history of cardiac hypertrophy.

In another embodiment, the present invention provides a method of preventing cardiac hypertrophy and dilated cardiomyopathy in a subject in need thereof comprising inhibiting expression or activity of one or more miR-15 family members in heart cells of the subject. In yet a further embodiment, the present invention provides a method of inhibiting progression of cardiac hypertrophy in a subject in need thereof comprising inhibiting expression or activity of one or more miR-15 family members in heart cells of the subject. In further embodiments, the present invention provides a method of increasing exercise tolerance, reducing hospitalization, improving quality of life, decreasing morbidity, and/or decreasing mortality in a subject with heart failure or cardiac hypertrophy comprising inhibiting expression or activity of one or more miR-15 family members in heart cells of the subject.

Thus, the present invention provides methods for the treatment of cardiac hypertrophy, heart failure, or myocardial infarction utilizing inhibitors of miR-15 family members, such as miR-195, miR-15a, miR-15b, miR-16-1, miR-16-2, miR-424, and miR-497. Preferably, administration of an inhibitor of a miR-15 family member results in the improvement of one or more symptoms of cardiac hypertrophy, heart failure, or myocardial infarction in the subject, or in the delay in the transition from cardiac hypertrophy to heart failure. The one or more improved symptoms may be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, decreased wall tension, increased quality of life, and decreased disease related morbidity or mortality. In addition, use of inhibitors of miR-15 family members may prevent cardiac hypertrophy and its associated symptoms from arising. In one embodiment, administration of an inhibitor of one or more miR-15 family members to a subject suffering from myocardial infarction may reduce infarct size by decreasing the loss of heart cells. In another embodiment, cardiac function is stabilized in a subject suffering from myocardial infarction following administration of an inhibitor of one or more miR-15 family members.

Inhibition of microRNA function may be achieved by administering antisense oligonucleotides targeting a mature sequence of a miR-15 family member. The antisense oligonucleotides may be ribonucleotides or deoxyribonucleotides. Preferably, the antisense oligonucleotides have at least one chemical modification. Antisense oligonucleotides may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Preferable antisense oligonucleotides useful for inhibiting the activity of microRNAs are about 19 to about 25 nucleotides in length. Antisense oligonucleotides may comprise a sequence that is at least partially complementary to a mature miRNA sequence, e.g. at least about 75%, 80%, 85%, 90%, 95%, 96%, 97%, 98%, or 99% complementary to a mature miRNA sequence. In some embodiments, the antisense oligonucleotide may be substantially complementary to a mature miRNA sequence, that is at least about 95%, 96%, 97%, 98%, or 99% complementary to a target polynucleotide sequence. In one embodiment, the antisense oligonucleotide comprises a sequence that is 100% complementary to a mature miRNA sequence.

In some embodiments, the antisense oligonucleotides are antagomirs. "Antagomirs" are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a cholesterol or other moiety at its 3' end. Antagomirs suitable for inhibiting miRNAs may be about 15 to about 50 nucleotides in length, more preferably about 18 to about 30 nucleotides in length, and most preferably about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 95%, 96%, 97%, 98%, or 99% complementary to a target polynucleotide sequence. In other embodiments, the antagomirs are 100% complementary to the mature miRNA sequence.

Another approach for inhibiting the function of a miR-15 family member is administering an inhibitory RNA molecule having a double stranded region that is at least partially identical and partially complementary to a mature sequence of the miR-15 family member. The inhibitory RNA molecule may be a double-stranded, small interfering RNA (siRNA) or a short hairpin RNA molecule (shRNA) comprising a stem-loop structure. The double-stranded regions of the inhibitory RNA molecule may comprise a sequence that is at least partially identical and partially complementary, e.g. about 75%, 80%, 85%, 90%, 95%, 96%, 97%, 98%, or 99% identical and complementary, to the mature miRNA sequence. In some embodiments, the double-stranded regions of the inhibitory RNA comprise a sequence that is at least substantially identical and substantially complementary to the mature miRNA sequence. "Substantially identical and substantially complementary" refers to a sequence that is at least about 95%, 96%, 97%, 98%, or 99% identical and complementary to a target polynucleotide sequence. In other embodiments, the double-stranded regions of the inhibitory RNA molecule may contain 100% identity and complementarity to the target miRNA sequence.

The inhibitory nucleotide molecules described herein preferably target a mature sequence of one or more miR-15 family members (e.g. SEQ ID NOs: 7, 9, 11, 14, 16, and 20) or a star sequence of one or more miR-15 family members (e.g. SEQ ID NOs: 8, 10, 12, 13, 15, 17, and 21). In some embodiments, inhibitors of miR-15 family members are antagomirs comprising a sequence that is perfectly complementary to a mature sequence of a miR-15 family member. In one embodiment, an inhibitor of a miR-15 family member is an antagomir having a sequence that is partially or perfectly complementary to SEQ ID NO: 7, SEQ ID NO: 9, SEQ ID NO: 11, SEQ ID NO: 14, SEQ ID NO: 16, or SEQ ID NO: 20. In another embodiment, an inhibitor of a miR-15 family member is an antagomir having a sequence that is partially or perfectly complementary to SEQ ID NO: 8, SEQ ID NO: 10, SEQ ID NO: 12, SEQ ID NO: 13, SEQ ID NO: 15, SEQ ID NO: 17, or SEQ ID NO: 21.

In some embodiments, inhibitors of one or more miR-15 family members are chemically-modified antisense oligonucleotides. In one embodiment, an inhibitor of a miR-15 family member is a chemically-modified antisense oligonucleotide comprising a sequence substantially complementary to SEQ ID NO: 7, SEQ ID NO: 9, SEQ ID NO: 11, SEQ ID NO: 14, SEQ ID NO: 16, or SEQ ID NO: 20. In another embodiment, an inhibitor of a miR-15 family member is a chemically-modified antisense oligonucleotide comprising a sequence substantially complementary to SEQ ID NO: 8, SEQ ID NO: 10, SEQ ID NO: 12, SEQ ID NO: 13, SEQ ID NO: 15, SEQ ID NO: 17, or SEQ ID NO: 21. As used herein "substantially complementary" refers to a sequence that is at least about 95%, 96%, 97%, 98%, 99%, or 100% complementary to a target polynucleotide sequence (e.g. mature or precursor miRNA sequence).

Antisense oligonucleotides may comprise a sequence that is substantially complementary to a precursor miRNA sequence (pre-miRNA) for one or more miR-15 family members (e.g. pre-miR-195, pre-miR-497, pre-miR-424, pre-miR-15a, pre-miR-15b, pre-miR-16-1, or pre-miR-16-2). In some embodiments, the antisense oligonucleotide comprises a sequence that is substantially complementary to a sequence located outside the stem-loop region of the pre-miRNA sequence. In one embodiment, an inhibitor of a miR-15 family member is an antisense oligonucleotide having a sequence that is substantially complementary to a pre-miRNA sequence selected from the group consisting of SEQ ID NO:

1, SEQ ID NO: 2, SEQ ID NO: 3, SEQ ID NO: 4, SEQ ID NO: 5, SEQ ID NO: 6, and SEQ ID NO: 19.

In other embodiments of the invention, inhibitors of one or more miR-15 family members may be inhibitory RNA molecules, such as ribozymes, siRNAs, or shRNAs. In one embodiment, an inhibitor of a miR-15 family member is an inhibitory RNA molecule comprising a double-stranded region, wherein the double-stranded region comprises a sequence having 100% identity and complementarity to a mature sequence of a miR-15 family member (e.g. SEQ ID NOs: 7, 9, 11, 14, 16, and 20). In another embodiment, an inhibitor of a miR-15 family member is an inhibitory RNA molecule comprising a double-stranded region, wherein the double-stranded region comprises a sequence having 100% identity and complementarity to a star sequence of a miR-15 family member (e.g. SEQ ID NOs: 8, 10, 12, 13, 15, 17, and 21). In some embodiments, inhibitors of one or more miR-15 family members are inhibitory RNA molecules which comprise a double-stranded region, wherein said double-stranded region comprises a sequence of at least about 75%, 80%, 85%, 90%, 95%, 96%, 97%, 98%, or 99% identity and complementarity to a mature sequence of one or more miR-15 family members.

Multiple members of the miR-15 family (e.g. miR-15a, miR-15b, miR-16-1, miR-16-2, miR-195, miR-424, and miR-497) may be inhibited simultaneously by administering multiple inhibitors, wherein each inhibitor targets a separate miR-15 family member. For example, in some embodiments, at least two members of the miR-15 family are inhibited by administering two separate inhibitors. In other embodiments, at least three members of the miR-15 family are inhibited by administering three separate inhibitors. In still other embodiments, at least four members of the miR-15 family are inhibited by administering four separate inhibitors. In further embodiments, at least five members of the miR-15 family are inhibited by administering five separate inhibitors. In one embodiment, all six members of the miR-15 family are inhibited by administering six separate inhibitors.

In another embodiment, an inhibitor of miR-15 family function is a nucleic acid comprising one or more miR-15 binding sites. The seed region (AGCAGCAC; SEQ ID NO: 18) of all the miR-15 family members is highly conserved. Therefore, a nucleic acid comprising a binding site having substantial complementarity to the miR-15 seed sequence would bind all members of the miR-15 family. This approach has been analogized to the use of a sponge to "soak up" the effective miR-15 family members, thereby reducing the overall pool of miRNAs that could impact a given target sequence. The term "miR-15 binding site" as used herein refers to a nucleotide sequence that is capable of binding a mature sequence of miR-15a, miR-15b, miR-16-1, miR-16-2, miR-195, miR-424, miR-497, or combinations thereof. Preferably, a miR-15 binding site comprises a sequence that is substantially complementary to the miR-15 seed sequence. The seed sequence or seed region refers to nucleotides 2-8 of the 5' portion of the mature miRNA sequence. In one embodiment, the miR-15 binding site comprises the a sequence that is substantially complementary to of SEQ ID NO: 18. The inhibitory nucleic acid comprising one or more miR-15 binding sites may be from about 20 to about 500 nucleotides in length, about 25 to about 400 nucleotides in length, about 30 to about 300 nucleotides in length, about 40 to about 200 nucleotides in length, or about 50 to about 100 nucleotides in length. For example, the nucleic acid may be 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 500 nucleotides in length. The nucleic acid may contain 1, 2, 3, 4, 5, 6, 7, 8, 9, 10, 12, 15, or 20 miR-15 binding sites. The multiple miR-15 binding sites may be adjacent or may be separated by spacers of 1, 2, 3, 4, 5, 6, 7, 8, 9, 10 or more nucleotides.

In another embodiment, an expression vector may be used to deliver an inhibitor of one or more miR-15 family members to a cell or subject. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an inhibitor of one or more miR-15 family members comprises a promoter operably linked to a polynucleotide encoding an antisense oligonucleotide, wherein the sequence of the expressed antisense oligonucleotide is partially or perfectly complementary to a mature sequence of one or more miR-15 family members. The phrase "operably linked" or "under transcriptional control" as used herein means that the promoter is in the correct location and orientation in relation to a polynucleotide to control the initiation of transcription by RNA polymerase and expression of the polynucleotide. In another embodiment, an expression vector for expressing an inhibitor of one or more miR-15 family members comprises one or more promoters operably linked to a polynucleotide encoding a shRNA or siRNA, wherein the expressed shRNA or siRNA comprises a double stranded region that is identical and complementary or partially identical and partially complementary to a mature sequence of one or more miR-15 family members. "Partially identical and partially complementary" refers to a sequence that is at least about 75%, 80%, 85%, 90%, 95%, 96%, 97%, 98%, or 99% identical and complementary to a target polynucleotide sequence.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III.

In some embodiments, the human cytomegalovirus (CMV) immediate early gene promoter, the SV40 early promoter, the Rous sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the polynucleotide of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the polynucleotide of interest (e.g. inhibitor of miR-15 family members). This list is not intended to be exhaustive of all the possible elements involved in the promotion of gene expression but, merely, to be exemplary thereof.

Below is a list of viral promoters, cellular promoters/enhancers and inducible promoters/enhancers that could be used in combination with the polynucleotide of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe |

TABLE 1-continued

Promoter and/or Enhancer

| Promoter/Enhancer | References |
|---|---|
|  | et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the alpha7 integrin promoter (Ziober and Kramer, 1996), the brain natriuretic peptide promoter (LaPointe et al., 1996) and the alpha B-crystallin/small heat shock protein promoter (Gopal-Srivastava, 1995), alpha myosin heavy chain promoter (Yamauchi-Takihara et al., 1989) and the ANF promoter (LaPointe et al., 1988).

A polyadenylation signal may be included to effect proper polyadenylation of the gene transcript where desired. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the cells containing nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide (or other inhibitory polynucleotide) that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

The typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing inhibitors of miR-15 family members in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a polynucleotide of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular polynucleotide of interest may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type (e.g. cardiac cell) by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the polynucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877, 302, 6,008,336, 6,077,835, 5,972,901, 6,200,801, and 5,972, 900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

The present invention also includes methods for scavenging or clearing inhibitors of miR-15 family members following treatment. The method may comprise overexpressing hybridization sites for inhibitors of the miR-15 family members in cardiac tissue. In one embodiment, the method comprises overexpression of hybridization sites for inhibitors of the miR-15 family members in cardiac muscle using a heart muscle specific promoter (e.g. α-MHC). In another embodiment, the hybridization site may comprise a sequence of a seed region from a miR-15 family member. In another embodiment, the hybridization site may comprise the sequence of SEQ ID NO: 18. In some embodiments, the hybridization site may contain a sequence that is complementary to a sequence from the 3'UTR of one or more targets of a miR-15 family member, such as FGF2, TGFb-induced factor 2, BCL9I, BCL2L, CDC25A, cyclin E1, cyclin D1, or cyclin D2.

In another embodiment of the invention, an inhibitor of one or more miR-15 family members is administered to the subject in combination with other therapeutic modalities. Current medical management of cardiac hypertrophy in the setting of a cardiovascular disorder includes the use of at least two types of drugs: inhibitors of the renin-angiotensin system and β-adrenergic blocking agents (Bristow, 1999). Therapeutic agents to treat pathologic hypertrophy in the setting of heart failure include angiotensin II converting enzyme (ACE) inhibitors and β-adrenergic receptor blocking agents (Eichhorn and Bristow, 1996). Other pharmaceutical agents that have been disclosed for treatment of cardiac hypertrophy include angiotensin II receptor antagonists (U.S. Pat. No. 5,604,251) and neuropeptide U antagonists (WO 98/33791).

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

Thus, in addition to the therapies described above, one may also provide to the subject more "standard" pharmaceutical cardiac therapies with the inhibitor of one or more miR-15 family members. Examples of other therapies include, without limitation, so-called "beta blockers," anti-hypertensives, cardiotonics, anti-thrombotics, vasodilators, hormone antagonists, iontropes, diuretics, endothelin receptor antagonists, calcium channel blockers, phosphodiesterase inhibitors, ACE inhibitors, angiotensin type 2 antagonists and cytokine blockers/inhibitors, and HDAC inhibitors. The combination therapy also may involve inhibiting the expression or activity of additional miRNAs involved in cardiac remodeling such as miR-499, miR-208, miR-208b and miR-21. Combination therapy may also include overexpression of particular microRNAs, such as miR-29.

Combinations may be achieved by contacting cardiac cells with a single composition or pharmacological formulation that includes an inhibitor of one or more miR-15 family members and a standard pharmaceutical agent, or by contacting the cell with two distinct compositions or formulations, at the same time, wherein one composition includes the inhibitor of a miR-15 family member and the other includes the standard pharmaceutical agent. Alternatively, the therapy using an inhibitor of a miR-15 family member may precede or follow administration of the other agent(s) by intervals ranging from minutes to weeks. In embodiments where the standard pharmaceutical agent and the inhibitor of a miR-15 family member are applied separately to the cell, one would generally ensure that a significant period of time did not expire between the time of each delivery, such that the pharmaceutical agent and inhibitor of a miR-15 family member would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an inhibitor of a miR-15 family member, or the other pharmaceutical agent will be desired. In this regard, various combinations may be employed. By way of illustration, where the inhibitor of a miR-15 family member is "A" and the other pharmaceutical agent is "B," the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are likewise contemplated.

Treatment regimens would vary depending on the clinical situation. However, long-term maintenance would appear to be appropriate in most circumstances. It also may be desirable to treat hypertrophy with inhibitors of miR-15 family members intermittently, such as within a brief window during disease progression.

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain embodiments, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof. Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate. Non-limiting examples of resins/bile acid sequesterants include cholestyramine (cholybar, questran), colestipol (colestid) and polidexide. Non-limiting examples of HMG CoA reductase inhibitors include lovastatin (mevacor), pravastatin (pravochol) or simvastatin (zocor). Non-limiting examples of nicotinic acid derivatives include nicotinate, acepimox, niceritrol, nicoclonate, nicomol and oxiniacic acid. Non-limiting examples of thyroid hormones and analogs thereof include etoroxate, thyropropic acid and thyroxine.

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin. A non-limiting example of an antiarteriosclerotic includes pyridinol carbamate.

In certain embodiments, administration of an agent that aids in the removal or prevention of blood clots may be combined with administration of a modulator, particularly in treatment of atherosclerosis and vasculature (e.g., arterial)

blockages. Non-limiting examples of antithrombotic and/or fibrinolytic agents include anticoagulants, anticoagulant antagonists, antiplatelet agents, thrombolytic agents, thrombolytic agent antagonists or combinations thereof. In certain embodiments, antithrombotic agents that can be administered orally, such as, for example, aspirin and wafarin (coumadin), are preferred.

Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Non-limiting examples of antiplatelet agents include aspirin, a dextran, dipyridamole (persantin), heparin, sulfinpyranone (anturane) and ticlopidine (ticlid).

Non-limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a patient is suffering from a hemorrhage or an increased likelihood of hemorrhaging, an agent that may enhance blood coagulation may be used. Non-limiting examples of blood coagulation promoting agents include thrombolytic agent antagonists and anticoagulant antagonists. Non-limiting examples of anticoagulant antagonists include protamine and vitamine K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

Non-limiting examples of antiarrhythmic agents include Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythmic agents.

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain embodiments, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Non-limiting examples of an agent that prolong repolarization, also known as a Class III antiarrhythmic agent, include amiodarone (cordarone) and sotalol (betapace).

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Non-limiting examples of miscellaneous antiarrhythmic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an alpha and beta adrenergic antagonist. Non-limiting examples of an alpha/beta blocker comprise labetalol (normodyne, trandate).

Non-limiting examples of anti-angiotensin II agents include angiotensin converting enzyme inhibitors and angiotensin II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotensin II receptor antagonist, an ANG receptor blocker or an ANG-II type-1 receptor blocker (ARBS), include angiocandesartan, eprosartan, irbesartan, losartan and valsartan.

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting examples of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain embodiments, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothizide, meticrane, metolazone, paraflutizide, polythizide, tetrachlormethiazide and trichlormethiazide. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril. Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todralazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide.

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Non-limiting examples of agents for the treatment of congestive heart failure include anti-angiotensin II agents, afterload-preload reduction treatment, diuretics and inotropic agents.

In certain embodiments, an animal patient that can not tolerate an angiotensin antagonist may be treated with a combination therapy. Such therapy may combine administration of hydralazine (apresoline) and isosorbide dinitrate (isordil, sorbitrate).

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular embodiments, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor. Inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

In certain embodiments, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

In another embodiment, the present invention provides a method of treating or preventing a musculoskeletal disorder in a subject in need thereof comprising (a) identifying a subject having or at risk of a musculoskeletal disorder; and (b) increasing the expression and/or activity of one or more miR-15 family members in skeletal muscle cells of said subject. The disorder may be selected from the group consisting of muscular dystrophy, disuse atrophy, muscle wasting in response to anti-gravity and denervation. Increasing the expression and/or activity may comprise administering said one or more miR-15 family members to said subject, optionally comprised within a lipid vehicle, or may comprise administering an expression vector that expresses said one or more miR-15 family members in said subject. The expression vector may be a viral expression vector, such as an adenoviral expression vector, or a non-viral expression vector, such as one comprised within a lipid vehicle. The method may further comprise a non-miR-15 family member therapy (i.e. another microRNA or other appropriate therapy).

The present invention also encompasses a pharmaceutical composition comprising an inhibitor of one or more miR-15 family members (e.g. miR-195, miR-497, miR-424, miR-15a, miR-15b, miR-16-1, and miR-16-2). The pharmaceutical composition may comprise any inhibitor of a miR-15 family member as described herein, such as an antagomir, an antisense oligonucleotide, an inhibitory RNA molecule, and a nucleic acid comprising one or more miR-15 binding sites. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of microRNA function or constructs expressing inhibitory nucleotides. Commercially available fat emulsions that are suitable for delivering the nucleic acids of the invention to tissues, such as cardiac muscle tissue, include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Buffers also will be employed when recombinant cells are introduced into a patient. Aqueous compositions of the present invention comprise an effective amount of the delivery vehicle or cells, dissolved or dispersed in a pharmaceutically acceptable carrier or aqueous medium. The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising miRNA inhibitors or expression constructs encoding inhibitory polynucleotides may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Any of the compositions described herein may be comprised in a kit. In a non-limiting example, an inhibitor of one or more miR-15 family members, such as an antagomir, is included in a kit. The kit may contain two or more, three or more, four or more, five or more, or six inhibitors for each miR-15 family member. By way of example, the kit may contain an inhibitor of miR-195 and an inhibitor of miR-15a. All possible combinations of inhibitors for miR-15 family members are contemplated by the invention. The kit may further include water and/or buffers to stabilize the inhibitory polynucleotides. The kit may also include one or more transfection reagent(s) to facilitate delivery of the miRNA inhibitors to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the miRNA inhibitors or that protect against their degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented. A kit may also include utensils or devices for administering the miRNA inhibitor by various administration routes, such as parenteral or catheter administration.

It is contemplated that such reagents are embodiments of kits of the invention. Such kits, however, are not limited to the particular items identified above and may include any reagent used for the manipulation or characterization of miRNA.

The present invention further comprises methods for identifying modulators of miR-15 family members. Identified inhibitors of the function of one or more miR-15 family members are useful in the prevention or treatment or reversal of cardiac hypertrophy or heart failure. Modulators (e.g. inhibitors) of miR-15 family members may be included in pharmaceutical compositions for the treatment of cardiac disorders according to the methods of the present invention.

These assays may comprise random screening of large libraries of candidate compounds; alternatively, the assays may be used to focus on particular classes of compounds selected with an eye towards structural attributes that are believed to make them more likely to inhibit the expression and/or function of miR-15 family members.

To identify a modulator of a miR-15 family member, one generally will determine the function of a miR-15 family member in the presence and absence of the candidate compound. For example, a method generally comprises:
(a) providing a candidate compound;
(b) admixing the candidate compound with a miR-15 family member;
(c) measuring activity of the miR-15 family member; and
(d) comparing the activity in step (c) with the activity in the absence of the candidate compound,
wherein a difference between the measured activities indicates that the candidate compound is a modulator of a miR-15 family member.
Assays also may be conducted in isolated cells, organs, or in living organisms.

Assessing the activity or expression of a miR-15 family member may comprise assessing the expression level of the miR-15 family member. Those in the art will be familiar with a variety of methods for assessing RNA expression levels including, for example, northern blotting or RT-PCR. Assessing the activity or expression of the miR-15 family member may comprise assessing the activity of the miR-15 family member. In some embodiments, assessing the activity of the miR-15 family member comprises assessing expression or activity of a gene regulated by the miR-15 family member. Genes regulated by miR-15 family members include, for example, FGF2, TGFb-induced factor 2, BCL9I, BCL2L, CDC25A, cyclin E1, cyclin D1, and cyclin D2. Those in the art will be familiar with a variety of methods for assessing the activity or expression of genes regulated by miR-15 family members. Such methods include, for example, northern blotting, RT-PCR, ELISA, or western blotting.

It will, of course, be understood that all the screening methods of the present invention are useful in themselves notwithstanding the fact that effective candidates may not be found. The invention provides methods for screening for such candidates, not solely methods of finding them.

As used herein the term "candidate substance" refers to any molecule that may potentially modulate the function of miR-15 family members. One will typically acquire, from various commercial sources, molecular libraries that are believed to meet the basic criteria for useful drugs in an effort to "brute force" the identification of useful compounds. Screening of such libraries, including combinatorially-generated libraries (e.g., antagomir libraries), is a rapid and efficient way to screen large number of related (and unrelated) compounds for activity. Combinatorial approaches also lend themselves to rapid evolution of potential drugs by the creation of second, third, and fourth generation compounds modeled on active, but otherwise undesirable compounds. Non-limiting examples of candidate compounds that may be screened according to the methods of the present invention are proteins, peptides, polypeptides, polynucleotides, oligonucleotides or small molecules. Modulators of miR-15 family members may also be agonists or inhibitors of upstream regulators of any one of the miR-15 family members.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

A technique for high throughput screening of compounds is described in WO 84/03564, which is herein incorporated by reference in its entirety. Large numbers of small antagomir compounds may be synthesized on a solid substrate, such as plastic pins or some other surface. Such molecules can be rapidly screening for their ability to hybridize to miR-15 family members.

The present invention also contemplates the screening of compounds for their ability to modulate expression and/or function of one or more miR-15 family members in cells. Various cell lines, including those derived from skeletal muscle cells, can be utilized for such screening assays, including cells specifically engineered for this purpose. Primary cardiac cells also may be used, as can the H9C2 cell line.

In vivo assays involve the use of various animal models of heart disease, including transgenic animals, that have been engineered to have specific defects, or carry markers that can be used to measure the ability of a candidate compound to reach and affect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to alteration of hypertrophic signaling pathways and physical symptoms of hypertrophy. Also, measuring toxicity and dose response can be performed in animals in a more meaningful fashion than in in vitro or in cyto assays.

In one embodiment, the present invention provides a method of regulating cardiac cell survival comprising administering to cardiac cells a modulator of one or more miR-15 family members. In another embodiment, the modulator is an agonist of the expression or activity of a miR-15 family member. In another embodiment, cardiac cell survival is decreased following administration of an agonist of a miR-15 family member. In another embodiment, the modulator of a miR-15 family member is an inhibitor of the expression or activity of a miR-15 family member. In still another embodiment, cardiac cell survival is increased following administration of an inhibitor of a miR-15 family member.

In a further embodiment, the present invention provides a method of regulating apoptosis of cardiac cells comprising administering to cardiac cells a modulator of one or more miR-15 family members. In another embodiment, the modulator is an agonist of the expression or activity of a miR-15 family member. In another embodiment, apoptosis of cardiac cells is increased following administration of an agonist of a miR-15 family member. In another embodiment, the modulator of a miR-15 family member is an inhibitor of the expression or activity of a miR-15 family member. In still another embodiment, apoptosis of cardiac cells is decreased following administration of an inhibitor of a miR-15 family member. In some embodiments, the expression of FGF2, TGFb-induced factor 2, BCL9I, BCL2L, CDC25A, cyclin E1, cyclin D1, or cyclin D2 is increased in a cell by contacting the cell with a miR-15 family inhibitor. In other embodiments, expression of FGF2, TGFb-induced factor 2, BCL9I, BCL2L, CDC25A, cyclin E1, cyclin D1, or cyclin D2 is decreased in a cell by contacting the cell with a miR-15 family agonist.

Thus, the present invention includes a method of regulating expression of FGF2, TGFb-induced factor 2, BCL9I, BCL2L, CDC25A, cyclin E1, cyclin D1, or cyclin D2 in a cell comprising contacting the cell with a modulator of a miR-15 family member. In one embodiment, the expression of FGF2, TGFb-induced factor 2, BCL9I, BCL2L, CDC25A, cyclin E1, cyclin D1, or cyclin D2 is decreased in the cell following administration of a miR-15 family agonist. In another embodiment, the expression of FGF2, TGFb-induced factor 2, BCL9I, BCL2L, CDC25A, cyclin E1, cyclin D1, or cyclin D2 is increased in the cell following administration of a miR-15 family inhibitor.

An agonist of a miR-15 family member may be a polynucleotide comprising a mature sequence or a star sequence from a miR-15 family member. In one embodiment, the polynucleotide comprises the sequence of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 20, or SEQ ID NO: 21. In another embodiment, the agonist of a miR-15 family member may be a polynucleotide comprising the pri-miRNA or pre-miRNA sequence for a miR-15 family member (e.g. pre-miR-195, pre-miR-497, pre-miR-424, pre-miR-15a, pre-miR-15b, pre-miR-16-1, or pre-miR-16-2). For example, in one embodiment, the agonist may be a polynucleotide comprising a sequence of SEQ ID NO: 1, SEQ ID NO: 2, SEQ ID NO: 3, SEQ ID NO: 4, SEQ ID NO: 5, SEQ ID NO: 6, or SEQ ID NO: 19. The polynucleotide comprising the a mature sequence of a miR-15 family member may be single stranded or double stranded. The polynucleotides may contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-15 family member sequence is conjugated to cholesterol. In another embodiment, the agonist of a miR-15 family member may be an agent distinct from the miR-15 family member that acts to increase, supplement, or replace the function of the miR-15 family member. In another embodiment, the miR-15 family agonist may be expressed in vivo from a vector.

In one embodiment, the present invention provides a method for treating pathologic cardiac hypertrophy, heart failure, or myocardial infarction in a subject in need thereof comprising: identifying a subject having cardiac hypertrophy, heart failure, or myocardial infarction; and administering an inhibitor of one or more miR-15 family members to the subject. In certain embodiments of the invention the miR-15 family inhibitor may be identified by a method comprising: (a) contacting a cell with a candidate compound; (b) assessing activity or expression of a miR-15 family member; and (c) comparing the activity or expression in step (b) with the activity or expression in the absence of the candidate compound, wherein a reduction in the activity or expression of the miR-15 family member in the cell contacted with the candidate compound compared to the activity or expression in the cell in the absence of the candidate compound indicates that the candidate compound is an inhibitor of the miR-15 family member.

A particular embodiment of the present invention provides transgenic animals that lack one or both functional alleles of a miR-15 family member. Also, transgenic animals that express miR-15 family members under the control of an inducible, tissue selective or a constitutive promoter, recombinant cell lines derived from such animals, and transgenic embryos may be useful in determining the exact role that the miR-15 family member plays in the development and differentiation of cardiomyocytes and in the development of pathologic cardiac hypertrophy and heart failure. Furthermore, these transgenic animals may provide an insight into heart development. The use of constitutively expressed miR-15 family members provides a model for over- or unregulated expression. Also, transgenic animals that are "knocked out" for one or more miR-15 family members, in one or both alleles, are contemplated.

In a general embodiment, a transgenic animal is produced by the integration of a given transgene into the genome in a manner that permits the expression of the transgene. Methods for producing transgenic animals are generally described by Wagner and Hoppe (U.S. Pat. No. 4,873,191; incorporated herein by reference), and Brinster et al. (1985; incorporated herein by reference).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are described in Palmiter et al. (1982); and in Sambrook et al. (2001).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by C02 asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involves the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "cardiac hypertrophy" refers to the process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and thus studies aimed at understanding the molecular mechanisms of cardiac hypertrophy could have a significant impact on human health.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

The term "β-adrenergic receptor antagonist" refers to a chemical compound or entity that is capable of blocking, either partially or completely, the beta (β) type of adrenoreceptors (i.e., receptors of the adrenergic system that respond to catecholamines, especially norepinephrine). Some β-adrenergic receptor antagonists exhibit a degree of specificity for one receptor subtype (generally $β_1$); such antagonists are termed "$β_1$-specific adrenergic receptor antagonists" and "β$_2$-specific adrenergic receptor antagonists." The term β-adrenergic receptor antagonist" refers to chemical compounds that are selective and non-selective antagonists. Examples of β-adrenergic receptor antagonists include, but are not limited to, acebutolol, atenolol, butoxamine, carteolol, esmolol, labetolol, metoprolol, nadolol, penbutolol, propanolol, and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

The terms "angiotensin-converting enzyme inhibitor" or "ACE inhibitor" refer to a chemical compound or entity that is capable of inhibiting, either partially or completely, the enzyme involved in the conversion of the relatively inactive angiotensin I to the active angiotensin II in the rennin-angiotensin system. In addition, the ACE inhibitors concomitantly inhibit the degradation of bradykinin, which likely significantly enhances the antihypertensive effect of the ACE inhibitors. Examples of ACE inhibitors include, but are not limited to, benazepril, captopril, enalopril, fosinopril, lisinopril, quiapril and ramipril. The use of derivatives of known ACE inhibitors is encompassed by the methods of the present invention. Indeed any compound, which functionally behaves as an ACE inhibitor, is encompassed by the methods of the present invention.

As used herein, the term "genotypes" refers to the actual genetic make-up of an organism, while "phenotype" refers to physical traits displayed by an individual. In addition, the "phenotype" is the result of selective expression of the genome (i.e., it is an expression of the cell history and its response to the extracellular environment). Indeed, the human genome contains an estimated 30,000-35,000 genes. In each cell type, only a small (i.e., 10-15%) fraction of these genes are expressed.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The following examples are included to further illustrate various aspects of the invention. It should be appreciated by those of skill in the art that the techniques disclosed in the examples which follow represent techniques and/or compositions discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Regulation of Cardiac Hypertrophy and Heart Failure by Stress-Responsive miRNAs

In light of their involvement in modulating cellular phenotypes, the inventors have hypothesized that miRNAs may play a role in regulating the response of the heart to cardiac stress, which is known to result in transcriptional and translational changes in gene expression. To investigate the potential involvement of miRNAs in cardiac hypertrophy, a side-by-side miRNA microarray analysis was performed in two established mouse models of cardiac hypertrophy, using a microarray that represented 186 different miRNAs. Mice that were subjected to thoracic aortic banding (TAB), which induces hypertrophy by increased afterload on the heart (Hill et al., 2000), were compared to sham operated animals. In a second model, transgenic mice expressing activated calcineurin (CnA) in the heart, which results in a severe, well-characterized form of hypertrophy (Molkentin et al., 1998), were compared to wild-type littermates (FIG. 1A). RNA isolated from hearts of mice subjected to TAB showed increased expression of 27 miRNAs compared to sham-operated controls, and CnA Tg mice showed increased expression of 33 miRNAs compared with non-transgenic littermate controls, of which 21 were up-regulated in both models. Similarly, TAB and CnA-induced hypertrophy were accompanied by reduced expression of 15 and 14 miRNAs, respectively, of which 7 miRNAs were down-regulated in common (FIG. 1B). Northern analysis of expression of these miRNAs and previous microarray analyses (Barad et al., 2004; Sempere et al., 2004; Shingara et al., 2005; Babak et al., 2004; Liu et al., 2004) indicate that they are expressed in a wide range of tissues.

Based on their relative expression levels, conservation of human, rat and mouse sequences, and levels of expression during hypertrophy, the inventors focused on 11 up- and 5 down-regulated miRNAs. Northern blot analysis of RNA isolated from cardiac tissue from WT and CnA Tg animals confirmed an increased expression of miR-21, miR-23, miR-24, miR-125b, miR-195, miR-199a, and miR-214, and decreased expression of miR-29c, miR-93, miR-150 and miR-181b (FIG. 1C). Collectively, these data indicate that distinct miRNAs are regulated during cardiac hypertrophy, suggesting the possibility that they might function as modulators of this process.

Figure 2:
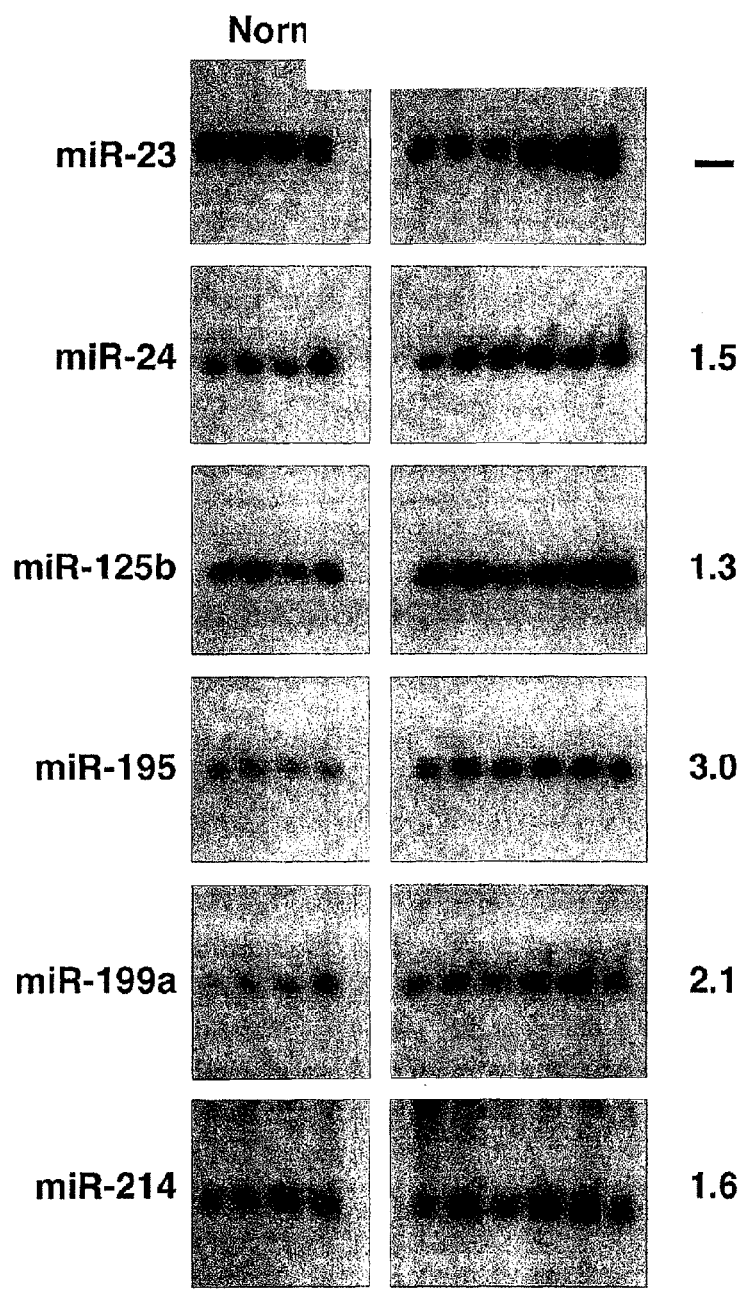
FIG. 2. miRNA expression in human heart failure. Northern blot analysis of miRNAs in 4 normal and 6 failing human hearts. The average fold-change of each miRNA in the failing samples is shown at the right.

Ventricular hypertrophy develops in response to numerous forms of cardiac stress and often leads to heart failure in humans (Arad et al., 2002). Northern blot analysis of the hypertrophy-regulated miRNAs in idiopathic end-stage failing human hearts showed increased expression of miR-24, miR-125b, miR-195, miR-199a and miR-214, while the expression for miR-23 appeared to be variable within the non-failing and failing groups (FIG. 2). No change in expression of miR-21, miR-27, miR-29c, miR-93, miR-150 and miR-181b was found (data not shown). Thus, the altered pattern of miRNA expression in the failing human heart overlapped with that of the hypertrophic mouse heart, suggesting that these miRNAs represent a molecular signature of adverse cardiac remodeling.

Example 2

Cardiac Over-Expression of miR-195 is Sufficient to Drive Cardiac Hypertrophy

Figure 3:
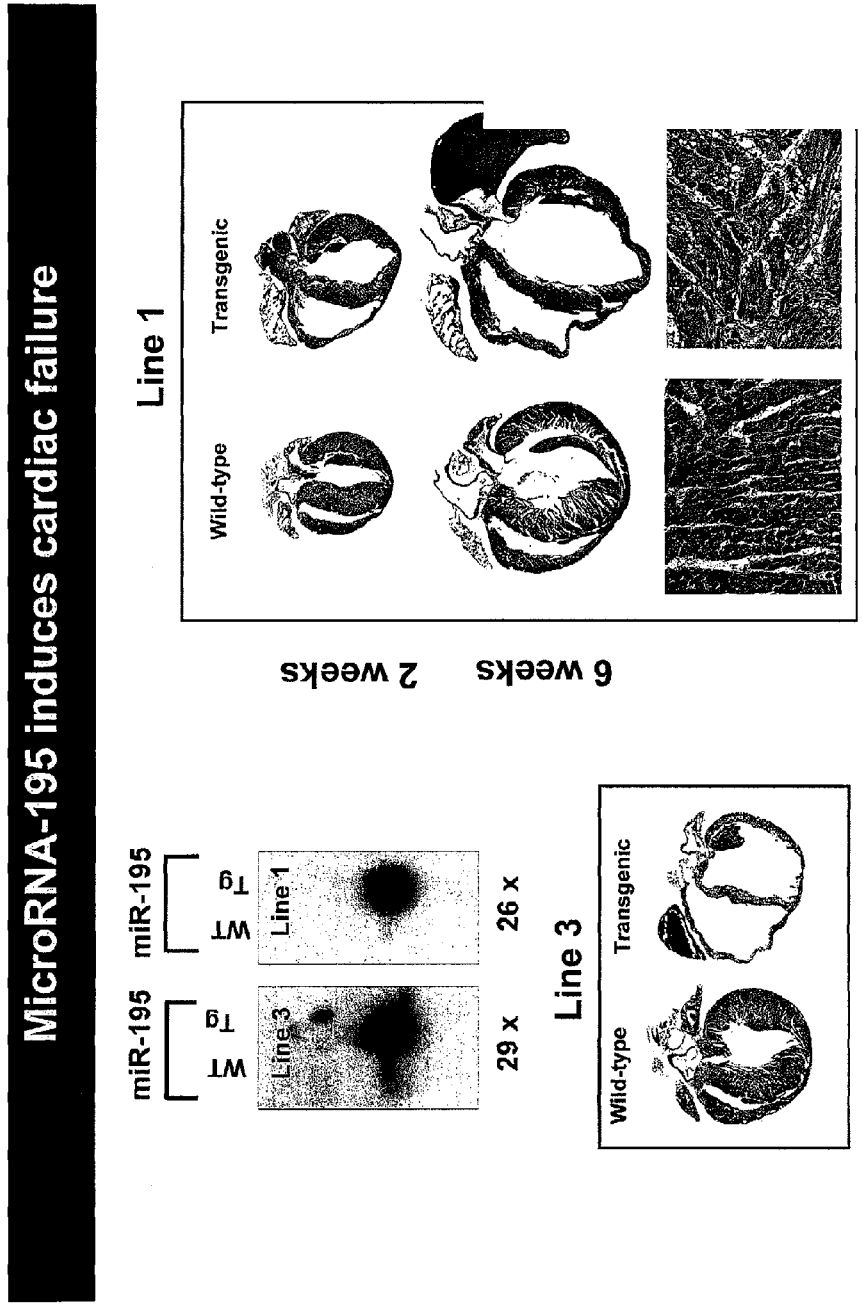
FIG. 3. Cardiac specific over-expression of miRNA 195 is sufficient to drive cardiomyopathy. H&E stained sections of hearts from wild-type (WT) and two different lines of miR-195 transgenic (Tg) animals. miRNA-195 Tg line 3 animals died two weeks after birth due to cardiac dilation. Northern blot analysis on hearts from WT and miR-195 transgenic lines 1 and 3 confirming a 26.5-fold and 29.2-fold cardiac specific miRNA over-expression, respectively.

MiR-24, miR-195 and miR-214 were overexpressed specifically in the heart under the control of the α-myosin heavy chain (MHC) promoter. F1 offspring could not be obtained for miR-24, suggesting that cardiac over-expression of this miRNA causes embryonic lethality. Since all offspring of the miR-195 transgenic (Tg) line 3 died in the first two weeks after birth due to heart failure (FIG. 3), the Tg line 1 for miR-195, which was viable, was used for further studies. Northern blot analysis showed miR-195 to be expressed at levels ~25-fold above normal in Tg line 1 (FIG. 3). Overexpression of miR-195 initially induced cardiac growth with disorganization of cardiomyocytes, which progressed to a dilated phenotype by 6 weeks of age. Although there were some fibrotic lesions, the dramatic increase in size of individual myocytes in miR-195 Tg mice compared to wild-type (WT) was more striking (FIG. 3).

Figure 4:
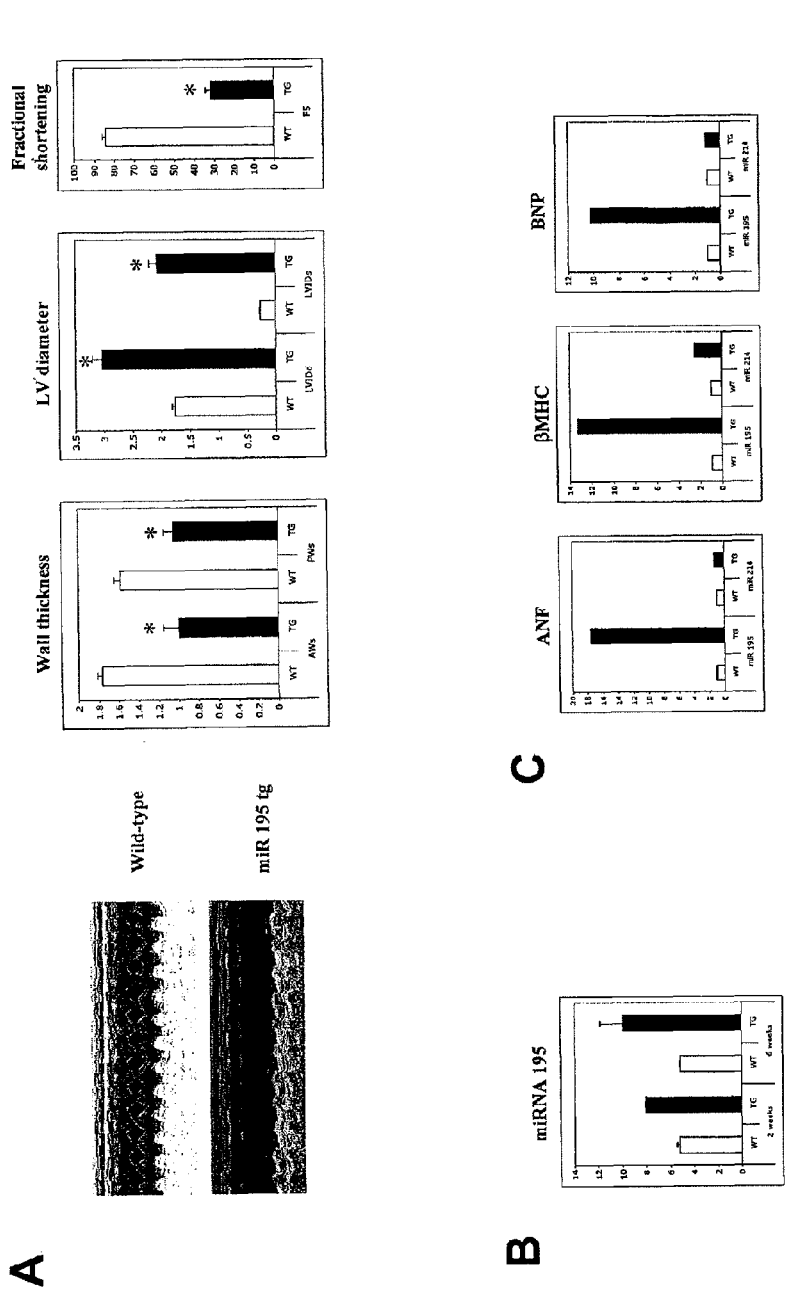
FIG. 4. Overexpression of miR-195 induces cardiac dysfunction due to cardiac growth. A. Echocardiographic analyses indicate miR-195 transgenic (Tg) mice show left ventricular (LV) dilation and wall thinning, resulting in a decreased fractional shortening compared to wild-type (WT) littermates. B. Heart weight to body weight ratio increases in response to cardiac specific overexpression of miR-195. C. Realtime PCR analysis shows an upregulation of hypertrophic genes in miR-195 Tg animals compared to WT animals (n=3). *P<0.05 compared to wild-type.

Echocardiography on 6 week-old animals showed that miR-195 Tg mice displayed thinning of the left ventricular walls (AWs and PWs), an increase in left ventricular diameter (LVIDd and LVIDs) and a deterioration in cardiac function, as indicated by decreased fractional shortening (FIG. 4A). Heart weight to body weight ratios were also dramatically increased in miR-195 Tg animals compared to WT littermates, indicating that over-expression of miR-195 was sufficient to stimulate cardiac growth (FIG. 4B). Real-time PCR analysis on cardiac tissue from miR-195 Tg animals compared to their WT littermates, revealed dramatic up-regulation of the hypertrophic markers atrial natriuretic factor (ANF), b-type natriuretic protein (BNP) and β-myosin heavy chain (βMHC) in response to cardiac over-expression of miR-195 (FIG. 4C).

Figure 5:
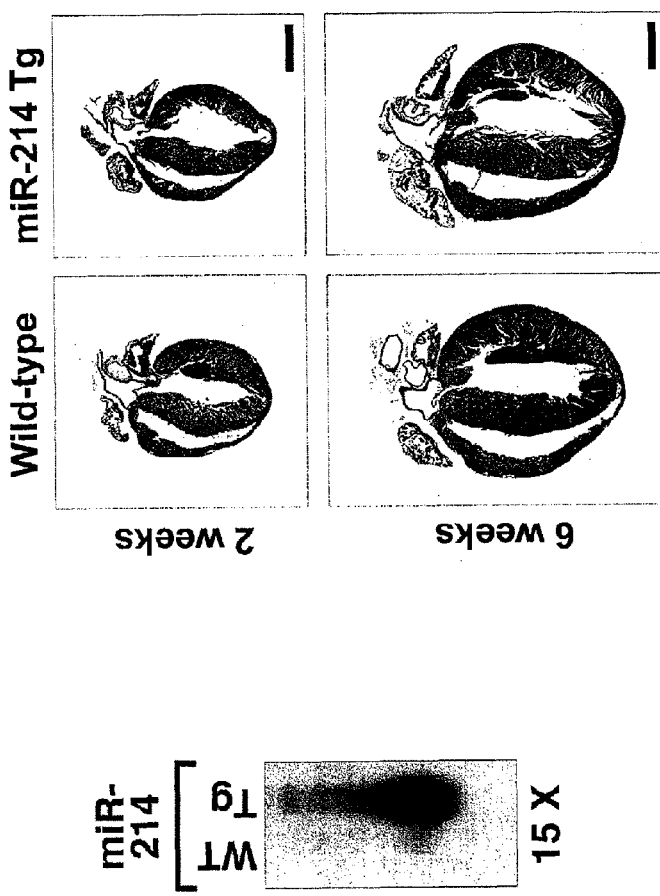
FIG. 5. Cardiac remodeling specific for miR-195. Overexpression of miR-195 induces cardiac growth at 2 weeks of age, which within 6 weeks progresses to a dilated phenotype. Cardiac over-expression of miR-214 has no phenotypic effect, indicating the specific effect of miR-195 on cardiac pathology. Scale bar equals 2 mm.

In contrast to the dramatic effects of overexpression of miR-195 on cardiac structure, function, and gene expression, cardiac over-expression of miR-214 at levels comparable to those of miR-195 had no phenotypic effect (FIGS. 4C and 5, and data not shown). Thus, the cardiac remodeling induced in the miR-195 Tg animals is specifically due to functional effects of this miRNA rather than a general non-specific effect resulting from miRNA over-expression. These results indicate that increased expression of miR-195 induces hypertrophic signaling leading to cardiac failure. Since miR-195 belongs to a small family of related miRNAs, the miR-15 family, other family members are also likely to participate in cardiac disease.

The ability of miR-195 to promote cardiac growth contrasts with that of miR-1, a muscle-specific miRNA that inhibits cardiac growth by suppressing the expression of the bHLH protein Hand2 (Zhao et al., 2005). miR-1 is highly expressed in the adult heart, but miR-195 is apparently capable of over-riding the inhibitory influence of miR-1 on cardiac growth.

It is especially interesting that overexpression in cardiomyocytes of the miRNAs that were down-regulated during hypertrophy caused an apparent reduction in cell size, an effect opposite than that evoked by the upregulated miRNAs. One interpretation of these results is that these miRNAs normally function to suppress growth and are therefore down-regulated to enhance hypertrophy.

miRNA-195 belongs to a small family of microRNAs, the miR-15 family, which contains miR-195, miR-16-1, miR-15a, miR-15b, miR-16-2, miR-424, and miR-497. Four of the miR-15 family members are expressed as three clustered transcripts (FIG. 6A). Using a variety of bioinformatics approaches, potential mRNA targets for miR-195 were identified. Several of the identified target mRNAs encode proteins involved in cell proliferation, survival and anti-apoptosis (FIG. 6B). One of the predicted targets for the miR-15 family is FGF2, which has been shown to promote cardiac repair (FIG. 7). All members of the miR-15 family are up-regulated in failing human hearts, indicating that this family of microRNAs plays a key role in pathological cardiac remodeling (FIG. 8). Since all the miR-15 family members share a conserved seed sequence, all miR-15 family members could be inhibited simultaneously by targeting the seed sequence. One such approach entails overexpression of a nucleic acid containing multiple binding sites, which comprise a sequence complementary to the seed sequence. The nucleic acid would "scavenge" or "sponge" all separate members because of their overlap in seed region and consequently overlap in target sequence (FIG. 8B) (Ebert et al., 2007).

All publications, patents, and patent applications discussed and cited herein are incorporated herein by reference in their entireties. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

X. REFERENCES

The following references, to the extent that they provide exemplary procedural or other details supplementary to those set forth herein, are specifically incorporated herein by reference.

U.S. Pat. No. 4,873,191
U.S. Pat. No. 5,604,251
U.S. Pat. No. 5,844,107
U.S. Pat. No. 5,877,302
U.S. Pat. No. 5,972,900
U.S. Pat. No. 5,972,901
U.S. Pat. No. 6,008,336
U.S. Pat. No. 6,077,835
U.S. Pat. No. 6,200,801
U.S. Publn. 20020150626
U.S. Publn. 20030032615
U.S. Publn. 20030203865
U.S. Publn. 20040048787
Abraham et al., *Mol. Med.,* 8:750-760, 2002.
Ambros, *Cell,* 113(6):673-676, 2003.
Angel et al., *Cell,* 49:729, 1987b.
Angel et al., *Mol. Cell. Biol.,* 7:2256, 1987a.
Arad et al., *Hum. Mol. genet.,* 11:2499-2506, 2002.
Atchison and Perry, *Cell,* 46:253, 1986.
Atchison and Perry, *Cell,* 48:121, 1987.

Babak et al., *RNA* 10:1813-1819, 2004.
Baichwal and Sugden, In: *Gene Transfer*, Kucherlapati (Ed.), Plenum Press, NY, 117-148, 1986.
Baldwin and Haddad, *J. Appl. Physiol.*, 90:345-357, 2001.
Banerji et al., *Cell*, 27(2 Pt 1):299-308, 1981.
Banerji et al., *Cell*, 33(3):729-740, 1983.
Barad et al., *Genome Res.* 14:2486-2494, 1997.
Barnes et al., *J. Biol. Chem.*, 272(17):11510-11517, 1997.
Benvenisty and Neshif, *Proc. Natl. Acad. Sci. USA*, 83(24):9551-9555, 1986.
Berkhout et al., *Cell*, 59:273-282, 1989.
Bhaysar et al., *Genomics*, 35(1):11-23, 1996.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brennecke et al., *Cell*, 113:25-36, 2003.
Brinster et al., *Proc. Natl. Acad. Sci. USA*, 82(13):4438-4442, 1985.
Bristow, *Cardiology*, 92:3-6, 1999.
Bulla and Siddiqui, *J. Virol.*, 62:1437, 1986.
Calin et al., *Proc. Natl. Acd. Sci. USA*, 99:15524-15529, 2002.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carrington et al. *Science*, 301(5631):336-338, 2003.
Celander and Haseltine, *J. Virology*, 61:269, 1987.
Celander et al., *J. Virology*, 62:1314, 1988.
Chandler et al., *Cell*, 33:489, 1983.
Chang and Karin, *Nature*, 410(6824):37-40, 2001.
Chang et al., *Biochim. Biophys. Acta*, 1092(2):153-160, 1991.
Chang et al., *Mol. Cell. Biol.*, 9:2153, 1989.
Chang et al., *Nature*, 430(7001):785-789, 2004.
Chatterjee et al., *Proc. Natl. Acad. Sci. USA*, 86:9114, 1989.
Chen and Okayama, *Mol. Cell Biol.*, 7(8):2745-2752, 1987.
Chen et al., *Mol. Cell Endocrinol.*, 162:45-55, 2000.
Chen et al., *Science*, 303(5654):83-86, 2004.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.
Durand et al., *Ann. Med.*, 27:311-317, 1995.
Ebert et al., *Nat. Methods*, 4:721-726, 2007.
Edbrooke et al., *Mol. Cell. Biol.*, 9:1908, 1989.
Edgerton and Roy, *J. Appl. Physiol.*, 89:1224-1231, 2000.
Edlund et al., *Science*, 230:912-916, 1985.
Eichhorn and Bristow, *Circulation*, 94:2285-2296, 1996.
EPO 0273085
Fechheimer, et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Fitts et al., *J. Appl. Physiol.*, 89:823-839, 2000.
Foecking and Hofstetter, *Gene*, 45(1):101-105, 1986.
Fraley et al., *Proc. Natl. Acad. Sci. USA*, 76:3348-3352, 1979.
Franz et al., *Cardioscience*, 5(4):235-43, 1994.
Friedman et al., *Genes Devel.*, 3:1314, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Gopal-Srivastava et al., *J. Mol. Cell. Biol.* 15(12):7081-7090, 1995.
Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36(1):59-74, 1977.
Greene et al., *Immunology Today*, 10:272, 1989
Grishok et al., *Cell*, 106:23-34, 2001.
Grosschedl and Baltimore, *Cell*, 41:885, 1985.
Grunhaus and Horwitz, *Seminar in Virology*, 3:237-252, 1992.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Natl. Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Natl. Acad. Sci. USA*, 90:2812-2816, 1993.
Hill et al., *Circulation*, 101:2863-2869, 2000.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hutvagner et al., *PLoS Biol.*, 2(4):E98, 2004.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Ito and Roeder, *Trends Endocrinol. Metab.*, 12:127-134, 2001.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Shenk, *Cell*, 13:181-188, 1978.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karlsson et al., *EMBO J.*, 5:2377-2385, 1986.
Katinka et al., *Cell*, 20:393, 1980.

Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Kelly et al., *J. Cell Biol.*, 129(2):383-396, 1995.
Kiledjian et al., *Mol. Cell. Biol.*, 8:145, 1988.
Kimura et al., *Dev. Growth Differ.* 39(3):257-265, 1997.
Kinugawa et al., *Circ. Res.*, 89:591-598, 2001.
Kinugawa et al., *J. Clin. Endocrinol. Metab.*, 86:5089-5090, 2001.
Kiriazis and Kranias, *Annu. Rev. Physiol.*, 62:321-351, 2000.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Krek et al., *Nat. Genet.*, 37:495-500, 2005.
Krenz and Robbins, *J. Am. Coll. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler et al., *Cell*, 38:483, 1984.
Kriegler et al., *Cell*, 53:45, 1988.
Kriegler and Botchan, *Mol. Cell. Biol.*, 3:325, 1983a.
Kriegler et al., In: *Gene Expression*, Alan Liss (Ed.), Hamer and Rosenberg, New York, 1983b.
Krützfeldt et al., *Nature*, 438:685-689, 2005.
Kuhl et al., *Cell*, 50:1057, 1987.
Kunz et al., *Nucl. Acids Res.*, 17:1121, 1989.
Lagos-Quintana et al., *Science*, 294(5543):853-858, 2001.
LaPointe et al., *Hypertension* 27(3 Pt 2):715-22, 1996.
LaPointe et al., *J. Biol. Chem.*, 263(19):9075-8, 1988.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lau et al., *Science*, 294(5543):858-862, 2001.
Le Gal La Salle et al., *Science*, 259:988-990, 1993.
Lee and Ambros, *Science*, 294(5543):862-864, 2001.
Lee et al., *Nature*, 294:228, 1981.
Lee et al., *Nucleic Acids Res.*, 12:4191-206, 1984.
Leung et al., *Proc. Natl. Acad. Sci. USA*, 48:18125-18130, 2006.
Levinson et al., *Nature*, 295:79, 1982.
Levrero et al., *Gene*, 101:195-202, 1991.
Lin et al., *Mol. Cell. Biol.*, 10:850, 1990.
Liu et al., *Proc Natl Acad Sci USA* 101:9740-9744, 2004.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Mann et al., *Cell*, 33:153-159, 1983.
Mansen et al., *Mol. Endocrinol.*, 15:2106-2114, 2001.
Markowitz et al., *J. Virol.*, 62:1120-1124, 1988.
McNeall et al., *Gene*, 76:81, 1989.
Meister and Tuschl, *Nature*, 431:343-9, 2004.
Miksicek et al., *Cell*, 46:203, 1986.
Molkentin et al., *Cell* 93:215-228, 1998.
Mordacq and Linzer, *Genes and Dev.*, 3:760, 1989.
Moreau et al., *Nucl. Acids Res.*, 9:6047, 1981.
Morkin, *Microsc. Res. Tech.*, 50:522-531, 2000.
Moss et al., *Biol. Chem.*, 271(49):31688-31694, 1996.
Muesing et al., *Cell*, 48:691, 1987.
Naya et al., *J Biol Chem*, 275(7):4545-4548, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Ojamaa et al., *Endocrinology*, 141:2139-2144, 2000.
Ondek et al., *EMBO J.*, 6:1017, 1987.
Ornitz et al., *Mol. Cell. Biol.*, 7:3466, 1987.
Palmiter et al., *Nature*, 300:611, 1982.
Pantos et al., *Horm. Metab. Res.*, 38:308-313, 2006.
Park et al., *Mol. Cell.*, 19:643-653, 2005.
Paskind et al., *Virology*, 67:242-248, 1975.
Pasquinelli and Ruvkun, *Ann. Rev. Cell Dev. Biol.*, 18:495-513, 2002.
Pavri et al., *Mol. Cell.*, 18:83-96, 2005.
PCT Appln. WO 0071096
PCT Appln. WO 84/03564
PCT Appln. WO 98/33791
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Physicians Desk Reference
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, $15^{th}$ ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell Biol.*, 10:689-695, 1990.
Rittling et al., *Nuc. Acids Res.*, 17:1619, 1989.
Rosen et al., *Cell*, 41:813, 1988.
Rosenfeld et al., *Science*, 252:431-434, 1991.
Rosenfeld, et al., *Cell*, 68:143-155, 1992.
Roux et al., *Proc. Natl. Acad. Sci. USA*, 86:9079-9083, 1989.
Sakai et al., *Genes and Dev.*, 2:1144, 1988.
Sambrook and Russell, Molecular Cloning: A Laboratory Manual $3^{rd}$ Ed., Cold Spring Harbor Laboratory Press, 2001.
Satake et al., *J. Virology*, 62:970, 1988.
Schaffner et al., *J. Mol. Biol.*, 201:81, 1988.
Schuyler and Yarbrough, *Basic Res. Cardiol.*, 85:481-494, 1990.
Searle et al., *Mol. Cell. Biol.*, 5:1480, 1985.
Sempere et al., *Genome Biol* 5:R13, 2004.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Shingara et al., *RNA* 11:1461-1470, 2005.

Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Stephens and Hentschel, *Biochem. J.,* 248:1, 1987.
Stratford-Perricaudet and Perricaudet, In: *Human Gene Transfer,* Eds, Cohen-Haguenauer and Boiron, John Libbey Eurotext, France, 51-61, 1991.
Stratford-Perricaudet et al., *Hum. Gene. Ther.,* 1:241-256, 1990.
Stuart et al., *Nature,* 317:828, 1985.
Sullivan and Peterlin, *Mol. Cell. Biol.,* 7:3315, 1987.
Swartzendruber and Lehman, *J. Cell. Physiology,* 85:179, 1975.
Takebe et al., *Mol. Cell. Biol.,* 8:466, 1988.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Temin, In: *Gene Transfer,* Kucherlapati (Ed.), NY, Plenum Press, 149-188, 1986.
The Merck Index, Eleventh Edition
Thiesen et al., *J. Virology,* 62:614, 1988.
Top et al., *J. Infect. Dis.,* 124:155-160, 1971.
Treisman, *Cell,* 46(4):567-174, 1986.
Tronche et al., *Mol. Biol. Med.,* 7:173, 1990.
Tronche et al., *Mol. Cell Biol.,* 9(11):4759-4766, 1989.
Trudel and Constantini, *Genes and Dev.,* 6:954, 1987.
Tsika et al., *Am. J. Physiol. Cell Physiol.,* 283:C1761-C1775, 2002.
Tur-Kaspa et al., *Mol. Cell Biol.,* 6:716-718, 1986.
Tyndell et al., *Nuc. Acids. Res.,* 9:6231, 1981.
Vadaszova et al., *Physiol. Res.* 53(1):S57-61, 2004.
van Rooij et al., *Proc. Natl. Acad. Sci. USA,* 103(48):18255-18260, 2006.
Vannice and Levinson, *J. Virology,* 62:1305, 1988.
Varmus et al., *Cell,* 25:23-36, 1981.
Vasseur et al., *Proc Natl. Acad. Sci. USA,* 77:1068, 1980.
Wagner et al., *Proc. Natl. Acad. Sci. USA* 87(9):3410-3414, 1990.
Wang and Calame, *Cell,* 47:241, 1986.
Weber et al., *Cell,* 36:983, 1984.
Wei et al., *J. Endocrinol. Invest.,* 28:8-11, 2005.
Weinberger et al. *Mol. Cell. Biol.,* 8:988, 1984.
Winoto and Baltimore, *Cell,* 59:649, 1989.
Wong et al., *Gene,* 10:87-94, 1980.
Wu and Wu, *Adv. Drug Delivery Rev.,* 12:159-167, 1993.
Wu and Wu, *Biochemistry,* 27: 887-892, 1988.
Wu and Wu, *J. Biol. Chem.,* 262:4429-4432, 1987.
Xu et al., *Curr. Biol.,* 13:790-795, 2003.
Yamauchi-Takihara, et. al., *Proc. Natl. Acad. Sci. USA,* 86(10):3504-3508, 1989.
Yang and Russell, *Proc. Natl. Acad. Sci. USA,* 87:4144-4148, 1990.
Yao and Eghbali, *Circ. Res.* 71:831-839, 1992.
Young et al., In: *Handbook of Applied Therapeutics,* 7.1-7.12 and 9.1-9.10, 1989.
Yutzey et al., *Mol. Cell. Biol.,* 9:1397, 1989.
Zelenin et al., *FEBS Lett.,* 287(1-2):118-120, 1991.
Zeng et al., *Cancer Res.,* 62(13):3630-3635, 2002.
Zhao et al., *Nature,* 436:214-220, 2005.
Ziober and Kramer, *J. Bio. Chem.,* 271(37):22915-22, 1996.

What is claimed is:

1. A method of treating pathologic cardiac hypertrophy, heart failure, or myocardial infarction in a subject in need thereof comprising administering to said subject an inhibitor of two or more miR-15 family members, wherein the inhibitor is a nucleic acid comprising a sequence that is substantially complementary to the sequence of SEQ ID NO: 18, and wherein the expression or activity of said two or more miR-15 family members is reduced in the heart cells of the subject following administration of the inhibitor.

2. The method of claim 1, wherein the nucleic acid is an antisense oligonucleotide.

3. The method of claim 1, wherein said two or more miR-15 family members are selected from the group consisting of miR-15a, miR-15b, miR-16, miR-195, miR-424, and miR-497.

4. The method of claim 2, wherein the antisense oligonucleotide comprises a sequence that is at least partially complementary to a mature sequence of a miR-15 family member.

5. The method of claim 4, wherein the antisense oligonucleotide comprises a sequence that is at least partially complementary to a sequence selected from the group consisting of: SEQ ID NO: 7, SEQ ID NO: 9, SEQ ID NO: 11, SEQ ID NO: 14, SEQ ID NO: 16, and SEQ ID NO: 20.

6. The method of claim 1, wherein the inhibitor of two or more miR-15 family members is administered by parenteral, oral, subcutaneous, intravenous, intramuscular, intradermal, intraperitoneal, transdermal, sustained release, controlled release, delayed release, suppository, catheter, or sublingual administration or direct injection into cardiac tissue.

7. The method of claim 1, further comprising administering to said subject a second therapy.

8. The method of claim 7, wherein said second therapy is selected from the group consisting of a beta blocker, an ionotrope, a diuretic, ACE-I, AII antagonist, BNP, a Ca++-blocker, an endothelin receptor antagonist, and an HDAC inhibitor.

9. The method of claim 1, wherein one or more symptoms of pathologic cardiac hypertrophy, heart failure, or myocardial infarction is improved in the subject following administration of the inhibitor of two or more miR-15 family members.

10. The method of claim 2, wherein the antisense oligonucleotide has at least one chemical modification.

11. The method of claim 10, wherein said chemical modification is a sugar modification or a backbone modification.

12. The method of claim 10, wherein said chemical modification is a locked nucleic acid.

13. The method of claim 2, wherein said antisense oligonucleotide is about 19 to about 25 nucleotides in length.

14. The method of claim 2, wherein said antisense oligonucleotide is about 15 nucleotides in length.

15. The method of claim 9, wherein said improved symptoms include increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, decreased wall tension, and reduction in infarct size.

16. The method of claim 11, wherein the sugar modification is a 2'-O-alkyl, 2'-O-methyl, 2'-O-methoxyethyl, 2'-fluoro, or 4'-thio modification.

17. The method of claim 11, wherein the backbone modification is a phosphorothioate linkage.

18. The method of claim 1, wherein the nucleic acid consists of a sequence that is complementary to the sequence of SEQ ID NO: 18.

19. The method of claim 1, wherein the expression or activity of three or more miR-15 family members is reduced in the heart cells of the subject following administration of the inhibitor.

20. The method of claim 1, wherein the expression or activity of all miR-15 family members is reduced in the heart cells of the subject following administration of the inhibitor.

21. The method of claim 1, wherein the nucleic acid comprises a sequence that is fully complementary to the sequence of SEQ ID NO: 18.

22. The method of claim 5, wherein the antisense oligonucleotide comprises a sequence that is at least 85% complementary to a sequence selected from the group consisting of:

SEQ ID NO: 7, SEQ ID NO: 9, SEQ ID NO: 11, SEQ ID NO: 14, SEQ ID NO: 16, and SEQ ID NO: 20.

23. The method of claim 5, wherein the antisense oligonucleotide comprises a sequence that is at least 95% complementary to a sequence selected from the group consisting of: SEQ ID NO: 7, SEQ ID NO: 9, SEQ ID NO: 11, SEQ ID NO: 14, SEQ ID NO: 16, and SEQ ID NO: 20.

24. The method of claim 1, wherein the nucleic acid comprises two or more binding sites, and wherein each binding site comprises a sequence that is substantially complementary to the sequence of SEQ ID NO: 18.

25. The method of claim 24, wherein each binding site comprises a sequence that is fully complementary to the sequence of SEQ ID NO: 18.

26. The method of claim 24, wherein the nucleic acid is expressed from a vector under the control of a cardiac-specific promoter.

27. The method of claim 26, wherein the cardiac-specific promoter is an alpha myosin heavy chain promoter.

* * * * *

UNITED STATES PATENT AND TRADEMARK OFFICE
CERTIFICATE OF CORRECTION

| | | |
|---|---|---|
| PATENT NO. | : 8,513,209 B2 | Page 1 of 1 |
| APPLICATION NO. | : 12/742233 | |
| DATED | : August 20, 2013 | |
| INVENTOR(S) | : Eric Olson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 93 days.

Signed and Sealed this
Twenty-seventh Day of January, 2015

Michelle K. Lee
*Deputy Director of the United States Patent and Trademark Office*

```
                           SEQUENCE LISTING

<160> NUMBER OF SEQ ID NOS: 21

<210> SEQ ID NO 1
<211> LENGTH: 87
<212> TYPE: RNA
<213> ORGANISM: Homo sapiens

<400> SEQUENCE: 1
agcuucccug gcucuagcag cacagaaaua uuggcacagg gaagcgaguc ugccaauauu      60
ggcugugcug cuccaggcag gguggug                                         87

<210> SEQ ID NO 2
<211> LENGTH: 112
<212> TYPE: RNA
<213> ORGANISM: Homo sapiens

<400> SEQUENCE: 2
ccaccccggu ccugcucccg ccccagcagc acacuguggu uuguacggca cuguggccac      60
guccaaacca cacuguggug uuagagcgag ggugggggag gcaccgccga gg             112

<210> SEQ ID NO 3
<211> LENGTH: 89
<212> TYPE: RNA
<213> ORGANISM: Homo sapiens

<400> SEQUENCE: 3
gucagcagug ccuuagcagc acguaaauau uggcguuaag auucuaaaau uaucuccagu      60
auuaacugug cugcugaagu aagguugac                                       89
```

```
<210> SEQ ID NO 4
<211> LENGTH: 81
<212> TYPE: RNA
<213> ORGANISM: Homo sapiens

<400> SEQUENCE: 4
guuccacucu agcagcacgu aaauauuggc guagugaaau auauauuaaa caccaauauu    60
acugugcugc uuuaguguga c                                              81

<210> SEQ ID NO 5
<211> LENGTH: 83
<212> TYPE: RNA
<213> ORGANISM: Homo sapiens

<400> SEQUENCE: 5
ccuuggagua aaguagcagc acauaauggu uugugauuu ugaaaaggug caggccauau     60
ugugcugccu caaaaauaca agg                                            83

<210> SEQ ID NO 6
<211> LENGTH: 98
<212> TYPE: RNA
<213> ORGANISM: Homo sapiens

<400> SEQUENCE: 6
uugaggccuu aaaguacugu agcagcacau caugguuuac augcuacagu caagaugcga    60
aucauuauuu gcugcucuag aaauuuaagg aaauucau                            98

<210> SEQ ID NO 7
<211> LENGTH: 21
<212> TYPE: RNA
<213> ORGANISM: Homo sapiens

<400> SEQUENCE: 7
uagcagcaca gaaauauugg c                                              21

<210> SEQ ID NO 8
<211> LENGTH: 22
<212> TYPE: RNA
<213> ORGANISM: Homo sapiens

<400> SEQUENCE: 8
ccaauauugg cugugcugcu cc                                             22

<210> SEQ ID NO 9
<211> LENGTH: 21
<212> TYPE: RNA
<213> ORGANISM: Homo sapiens

<400> SEQUENCE: 9
cagcagcaca cugugguuug u                                              21

<210> SEQ ID NO 10
<211> LENGTH: 22
<212> TYPE: RNA
<213> ORGANISM: Homo sapiens

<400> SEQUENCE: 10
caaaccacac ugugguguua ga                                             22

<210> SEQ ID NO 11
<211> LENGTH: 22
<212> TYPE: RNA
```

<213> ORGANISM: Homo sapiens

<400> SEQUENCE: 11
uagcagcacg uaaauauugg cg                                      22

<210> SEQ ID NO 12
<211> LENGTH: 22
<212> TYPE: RNA
<213> ORGANISM: Homo sapiens

<400> SEQUENCE: 12
ccaguauuaa cugugcugcu ga                                      22

<210> SEQ ID NO 13
<211> LENGTH: 22
<212> TYPE: RNA
<213> ORGANISM: Homo sapiens

<400> SEQUENCE: 13
ccaauauuac ugugcugcuu ua                                      22

<210> SEQ ID NO 14
<211> LENGTH: 22
<212> TYPE: RNA
<213> ORGANISM: Homo sapiens

<400> SEQUENCE: 14
uagcagcaca uaaugguuug ug                                      22

<210> SEQ ID NO 15
<211> LENGTH: 22
<212> TYPE: RNA
<213> ORGANISM: Homo sapiens

<400> SEQUENCE: 15
caggccauau ugugcugccu ca                                      22

<210> SEQ ID NO 16
<211> LENGTH: 22
<212> TYPE: RNA
<213> ORGANISM: Homo sapiens

<400> SEQUENCE: 16
uagcagcaca ucaugguuua ca                                      22

<210> SEQ ID NO 17
<211> LENGTH: 22
<212> TYPE: RNA
<213> ORGANISM: Homo sapiens

<400> SEQUENCE: 17
cgaaucauua uuugcugcuc ua                                      22

<210> SEQ ID NO 18
<211> LENGTH: 8
<212> TYPE: RNA
<213> ORGANISM: Homo sapiens

<400> SEQUENCE: 18 agcagcac                                                       8

<210> SEQ ID NO 19
<211> LENGTH: 98
<212> TYPE: RNA

```
<213> ORGANISM: Homo sapiens

<400> SEQUENCE: 19
cgaggggaua cagcagcaau ucauguuuug aaguguucua aaugguucaa aacgugaggc      60
gcugcuauac ccccucgugg ggaagguaga aggugggg                              98

<210> SEQ ID NO 20
<211> LENGTH: 22
<212> TYPE: RNA
<213> ORGANISM: Homo sapiens

<400> SEQUENCE: 20
cagcagcaau ucauguuuug aa                                               22

<210> SEQ ID NO 21
<211> LENGTH: 21
<212> TYPE: RNA
<213> ORGANISM: Homo sapiens

<400> SEQUENCE: 21
caaaacguga ggcgcugcua u                                                21
```